(12) United States Patent
Fujibe et al.

(10) Patent No.: US 8,835,580 B2
(45) Date of Patent: *Sep. 16, 2014

(54) CATALYST FOR NORBORNENE MONOMER POLYMERIZATION AND METHOD FOR PRODUCING NORBORNENE POLYMER

(75) Inventors: Satoshi Fujibe, Oita (JP); Nobuyuki Kibino, Oita (JP)

(73) Assignee: Showa Denko K.K., Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 13/824,221

(22) PCT Filed: Oct. 25, 2011

(86) PCT No.: PCT/JP2011/074547
§ 371 (c)(1),
(2), (4) Date: Jun. 3, 2013

(87) PCT Pub. No.: WO2012/057135
PCT Pub. Date: May 3, 2012

(65) Prior Publication Data
US 2013/0261271 A1    Oct. 3, 2013

(30) Foreign Application Priority Data

Oct. 26, 2010  (JP) ................ 2010-239163

(51) Int. Cl.
*C08F 4/82*       (2006.01)
*C08F 4/80*       (2006.01)
*C08F 32/00*      (2006.01)

(52) U.S. Cl.
USPC ........ 526/169.1; 526/172; 526/145; 526/139; 526/134; 526/131; 526/281

(58) Field of Classification Search
USPC ........ 502/103; 556/138; 526/172, 161, 169.1, 526/281
See application file for complete search history.

(56) References Cited

U.S. PATENT DOCUMENTS

| 3,330,815 | A | | 7/1967 | Mckeon et al. | |
| 5,714,556 | A | * | 2/1998 | Johnson et al. | 526/135 |
| 6,103,920 | A | * | 8/2000 | Johnson et al. | 556/140 |
| 6,174,975 | B1 | * | 1/2001 | Johnson et al. | 526/172 |
| 8,163,860 | B2 | * | 4/2012 | Kaita et al. | 526/281 |
| 2005/0043494 | A1 | | 2/2005 | Goodall et al. | |
| 2009/0203948 | A1 | | 8/2009 | Gladysz et al. | |

FOREIGN PATENT DOCUMENTS

| EP | 0445755 A2 | 9/1991 |
| JP | 2001-072654 A | 3/2001 |
| JP | 2005-68424 A | 3/2005 |
| JP | 3678754 B2 | 8/2005 |
| JP | 2008-031304 A | 2/2008 |
| JP | 2008-517036 A | 5/2008 |
| JP | 2008-202003 A | 9/2008 |
| JP | 2010-024399 A | 2/2010 |
| JP | 2010-196045 A | 9/2010 |
| WO | 2006/064814 A1 | 6/2006 |

OTHER PUBLICATIONS

Yang et al. Organometallics 1993, 12, 3485-3494.*

(Continued)

*Primary Examiner* — Rip A. Lee
(74) *Attorney, Agent, or Firm* — Sughrue Mion, PLLC

(57) ABSTRACT

The invention relates to a catalyst for the polymerization of norbornene monomers comprising transition metal complex (A) represented by formula (1); and a method for producing a norbornene (co)polymer, especially a norbornene copolymer containing a monomer unit represented by formulae (2) and (3), wherein a norbornen monomer is homopolyzed or copolymerized in the presence of the polymerization catalyst. Preferable examples of the transition metal complex (A) include ($\pi$-allyl){4-(2,6-diisopropylphenylimino)-2-penten-2-olato-$\kappa^2$N,O}palladium and ($\pi$-allyl){4-(1-naphthylimino)-2-penten-2-olato-$\kappa^2$N,O}palladium. In the formulae, the symbols are as defined in the description. A norbornene (co)polymer which has excellent transparency, excellent heat resistance, excellently low water absorption and excellent electrical insulation characteristics can be efficiently produced by the present invention.

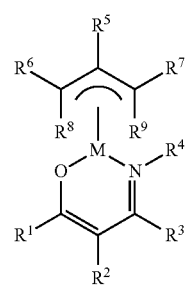

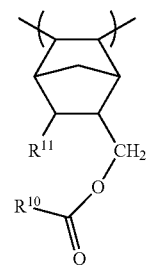

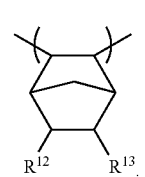

12 Claims, 8 Drawing Sheets

(56) References Cited

OTHER PUBLICATIONS

Lee et al. Bull. Korean Chem. Soc. 2009, 30, 636-646.*
Wang et al. European Polymer Journal 2006, 42, 322-327.*
Il Gu Jung et al., "Polymerization of 5-Norbornene-2-Methyl Acetate Catalyzed by Air-Stable Cationic ($n^3$-Substituted Allyl) Palladium Complexes of N-Heterocyclic Carbene", Journal of Organometallic Chemistry, 2009, pp. 297-303, vol. 694.
International Search Report for PCT/JP2011/074547 issued Nov. 29, 2011.
Extended European Search Report, dated Jul. 1, 2014, issued by the European Patent Office, in counterpart Application No. 11836268.0.
Lee, et al., "Novel and Efficient Palladium Complexes with B-Ketoiminate Ligands for the Polymerization of Norbornene", Bull. Korean Chem. Soc. 2009, vol. 30, No. 3, pp. 636-646.
Wang, et al., "Homo- and copolymerization of norbornene and norbornene derivative with Ni- and Pd-based B-ketoiminato complexes and MAO", European Polymer Journal 42 (2006), pp. 322-327.

* cited by examiner

CATALYST FOR NORBORNENE MONOMER POLYMERIZATION AND METHOD FOR PRODUCING NORBORNENE POLYMER

TECHNICAL FIELD

The present invention relates to a catalyst for polymerizing norbornene monomers, a method for producing a (co)polymer of norbornene monomers containing polar groups by using the catalyst, and a novel transition metal complex used in the catalyst.

BACKGROUND ART

Conventionally, addition polymers of cyclic olefins represented by norbornene polymers have been industrially used in the field of optical films and the like as an organic material being excellent in heat resistance and transparency. There have been various reports that such addition polymers of cyclic olefins can be produced by the addition polymerization of cyclic olefin monomer(s) using a catalyst containing transition metal compounds such as Ti, Zr, Cr, Co, Ni and Pd.

For example, the European Patent Publication No. 0445755 (Patent Document 1) reports that an addition homopolymer of norbornene having the number average molecular weight exceeding 1,000,000 can be produced by polymerizing a norbornene monomer alone by using a transition metal compound of elements belonging to five to ten groups of the periodic table as a main catalyst and methylaluminoxane (MAO) as a cocatalyst. However, polymerization of norbornene monomers containing polar groups which has higher difficulty in polymerization has not been conducted with this catalyst system, and there were concerns about the catalyst deactivation due to the influence of the polar group.

Meanwhile, U.S. Pat. No. 3,330,815 publication (Patent Document 2) discloses addition homopolymers of norbornene monomers containing polar groups and copolymers with norbornene using only dichlorobis(benzonitrile)palladium and allyl palladium chloride dimer as a catalyst. However, the patent has not reported an example where a polymer having a number average molecular weight exceeding 10,000. Also, the polymerization activity of the catalyst is low so that the production method was far from being an industrially useful method.

Moreover, Japanese Patent Publication No. 3678754 (WO96/37526; Patent Document 3) and JPA-2008-31304 publication (Patent Document 4) disclose a method for improving addition polymerization of a norbornene monomer alone containing polar group or copolymerization with norbornene. Though these methods improved both of polymerization activity and molecular weight of the obtained polymer by using a combination of allyl palladium chloride dimer with silver tetrafluoroborate and silver hexafluorophosphate as a catalyst, they only disclose copolymer having number average molecular weight less than 200,000 in examples and have not succeeded in producing copolymers having number average molecular weight of 200,000 or more which is required for mechanical properties to be developed to a practical level. In Table 1 of Patent Document 4, the number average molecular weight (Mn) entries and the weight average molecular weight (Mw) entries replace each other. It is obvious from that Mw/Mn values should be around 2.5, and it is clear that a copolymer having a number average molecular weight exceeding 200,000 did not exist if data in Table 1 are interpreted properly.

Contrary to these methods, International publication No. WO2006/064814 (US 2009/264608; Patent Document 5) discloses that addition copolymerization of norbornene containing polar group and norbornene can be efficiently performed by using compounds of transition metals belonging to eighth to tenth groups of the periodic table as a main catalyst in combination with a cocatalyst capable of producing a cationic transition metal compound through the reaction with the main catalyst to thereby obtain copolymers having high molecular weight. However, the norbornene compound disclosed by the publication has a structure wherein an ester group is directly introduced into a norbornene skeleton, and since the distance between the carbon-carbon double bonding site and the polar group is short, the norbornene compound easily forms coordinate bonding with a transition metal complex as a catalyst, resulting in catalyst deactivation. Accordingly, the method enables to produce a high molecular weight polymer by high activity in addition polymerization of norbornene alone. However, in case of using a norbornene monomer having a polar group, a copolymer having high molecular weight can be obtained but the catalyst activity of the copolymer was low.

As one of the methods to prevent the catalyst deactivation due to the coordinate bonding of norbornene with a transition metal complex, it is possible to extend the distance between the polymerizable carbon-carbon double bonding and a polar group (ester group). For example, "J. Organomet. Chem., 2009, 694, p. 297-303" (Non-patent Document 1) discloses a case of producing a homopolymer of a nobornene compound wherein a one methylene chain is introduced between the norbornene skeleton and an ester group, having a number average molecular weight of 100,000 or more, by using N-heterocyclic carbene complex. However, the polymerization activity is very low in the method and the method failed to obtain a polymer having a number average molecular weight exceeding 200,000.

From the description of these prior art documents, it can be seen that a high-activity catalyst system capable of obtaining a copolymer having a number average molecular weight as high as 200,000 or more in addition polymerization of norbornene monomers alone containing polar groups or addition copolymerization of norbornene monomers containing polar groups, which system experiences little deactivation, was previously unknown.

As discussed above, in a method for producing addition (co)polymers of norbornene containing polar groups, there have been no previous cases of a high activity catalyst which enables obtaining a norbornene (co)polymer having practical mechanical properties. Consequently, development of such a catalyst has been demanded.

PRIOR ART

Patent Documents

[Patent Document 1] European patent publication No. 0445755
[Patent Document 2] U.S. Pat. No. 3,330,815
[Patent Document 3] Japanese Patent No. 3678754
[Patent Document 4] Japanese Patent Publication No. 2008-31304
[Patent Document 5] International Publication No. WO2006/064814

Non-Patent Document

[Non-patent Document 1]
J. Organomet. Chem., 694, p. 297 (2009)

SUMMARY OF THE INVENTION

Problems to be Solved by the Invention

An objective of the present invention is to provide a high activity catalyst system which enables producing high-molecular weight addition (co)polymers of norbornene monomers containing polar groups and a method for efficiently producing the copolymers.

Methods to Solve the Problems

As a result of intensive studies to solve the above problems, the present inventors have found that a high-molecular weight addition copolymers of a norbornene monomers having polar groups can be produced efficiently by combining a catalyst system using a transition metal complex containing a π-allyl (η$^3$-allyl) ligand and a bidentate β-ketoimine ligand as a main catalyst and a norbornene compound in which a methylene chain is introduced between a norbornene skeleton and an ester group so as to distance the polymerizable carbon-carbon double bond from the polar group (ester group), and have completed the present invention.

That is, the present invention relates to the catalyst for the polymerization of norbornene monomers in [1] to [7]; the method for producing norbornene copolymer in [8] to [11] and the palladium complex in [12] to [13] as described below.

[1] A catalyst for the polymerization of norbornene monomers, comprising transition metal complex (A) represented by formula (1)

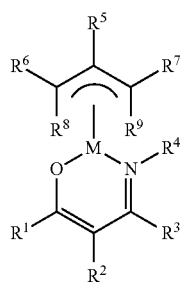

(1)

in the formula, M represents one transition metal selected from the elements belonging to eight, nine or ten group of the periodic table for 1991, and $R^1$, $R^2$ and $R^3$ independently represent a hydrogen atom or a hydrocarbon group having 1 to 20 carbon atoms; $R^4$ represents a hydrogen atom or a hydrocarbon group having 1 to 20 carbon atoms; $R^5$, $R^6$, $R^7$, $R^8$ and $R^9$ represent independently from each other a hydrogen atom, a halogen atom or a hydrocarbon group having 1 to 20 carbon atoms; and $R^5$, $R^6$, $R^7$, $R^8$ and $R^9$ may bond to each other to form a ring structure.

[2] The catalyst for the polymerization of norbornene monomers as described in [1] above, wherein M represents palladium (Pd) or nickel (Ni); $R^1$, $R^2$ and $R^3$ represents a hydrogen atom or an alkyl group having 1 to 6 carbon atoms; $R^4$ represents an aryl group having 6 to 20 carbon atoms; and all of $R^5$, $R^6$, $R^7$, $R^8$ and $R^9$ represent a hydrogen atom in formula (1).

[3] The catalyst for the polymerization of norbornene monomers as described in [2] above, wherein M represents palladium; $R^1$ and $R^3$ represent a methyl group; $R^2$ represents a hydrogen atom; and $R^4$ represent a 2,6-diisopropylphenyl group or a 1-naphthyl group in formula (1).

[4] The catalyst for the polymerization of norbornene monomers as described in any one of [1] to [3] above, comprising cocatalyst (B) as being an ionic compound which can generate a cationic transition metal compound by reacting with transition metal complex (A) and a phosphine ligand (C).

[5] The catalyst for the polymerization of norbornene monomers as described in [4] above, wherein cocatalyst (B) is trityl tetrakis(pentafluorophenyl)borate or N,N-dimethylanilinium tetrakis (pentafluorophenyl)borate.

[6] The catalyst for the polymerization of norbornene monomers as described in [4] above, wherein phosphine ligand (C) is trialkylphosphine.

[7] The catalyst for the polymerization of norbornene monomers as described in [6] above, wherein phosphine ligand (C) is triisopropylphosphine.

[8] A method for producing norbornene (co)polymers comprising homopolymerization of norbornene monomers alone or copolymerization of norbornene monomers in the presence of the catalyst as described in any one of [1] to [7] above.

[9] A method for producing norbornene copolymers comprising copolymerization of norbornene monomers and other vinyl monomers in the presence of the catalyst as described in any one of [1] to [7] above.

[10] A method for producing norbornene copolymers comprising monomer units represented by formulae (2) and (3)

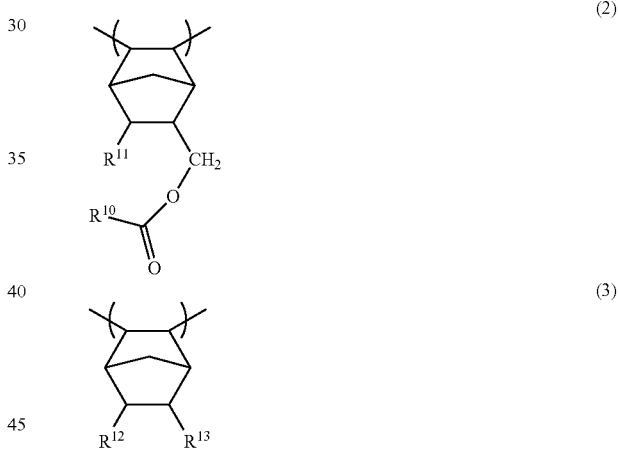

(in the formula, $R^{10}$ represents an alkyl group having 1 to 10 carbon atoms; and $R^{11}$, $R^{12}$ and $R^{13}$ independently represent a hydrogen atom or an alkyl group having 1 to 10 carbon atoms), comprising polymerization of norbornene monomers corresponding to the monomer unit represented by formulae (2) and (3) in the presence of the catalyst as described in any one of [1] to [7] above.

[11] The method for producing norbornene copolymers as described in [10] above, wherein the copolymers comprise a monomer unit represented by formulae (2) and (3) only.

[12] (π-allyl){4-(2,6-diisopropylphenylimino)-2-penten-2-olato-κ$^2$N,O}palladium.

[13] (π-allyl){4-(1-naphthylimino)-2-penten-2-olato-κ$^2$N,O}palladium.

Effects of the Invention

The present invention enables efficiently producing high-molecular weight addition copolymers of norbornene and norbornene monomers containing polar groups. The norbornene copolymer obtained by the present invention has excellent properties such as transparency, heat resistance, low water absorption and electric insulating property, and can be used for many applications such as optics application, application in medical treatment, electronic material application, packaging material application and structural material application.

Specifically, the copolymers can be used for optical molded products such as lenses and polarizing films; electric insulating materials for films, carrier tapes, film capacitors, flexible printed circuit boards, etc.; and medical containers such as press-through packages, infusion bags and chemical vials; food-packaging molded product such as plastic wraps and trays; casings for electric appliances; automobile interior parts such as an inner panel; building materials for a carport, glazing and the like; etc.

MODE FOR CARRYING OUT INVENTION

Figure 1:
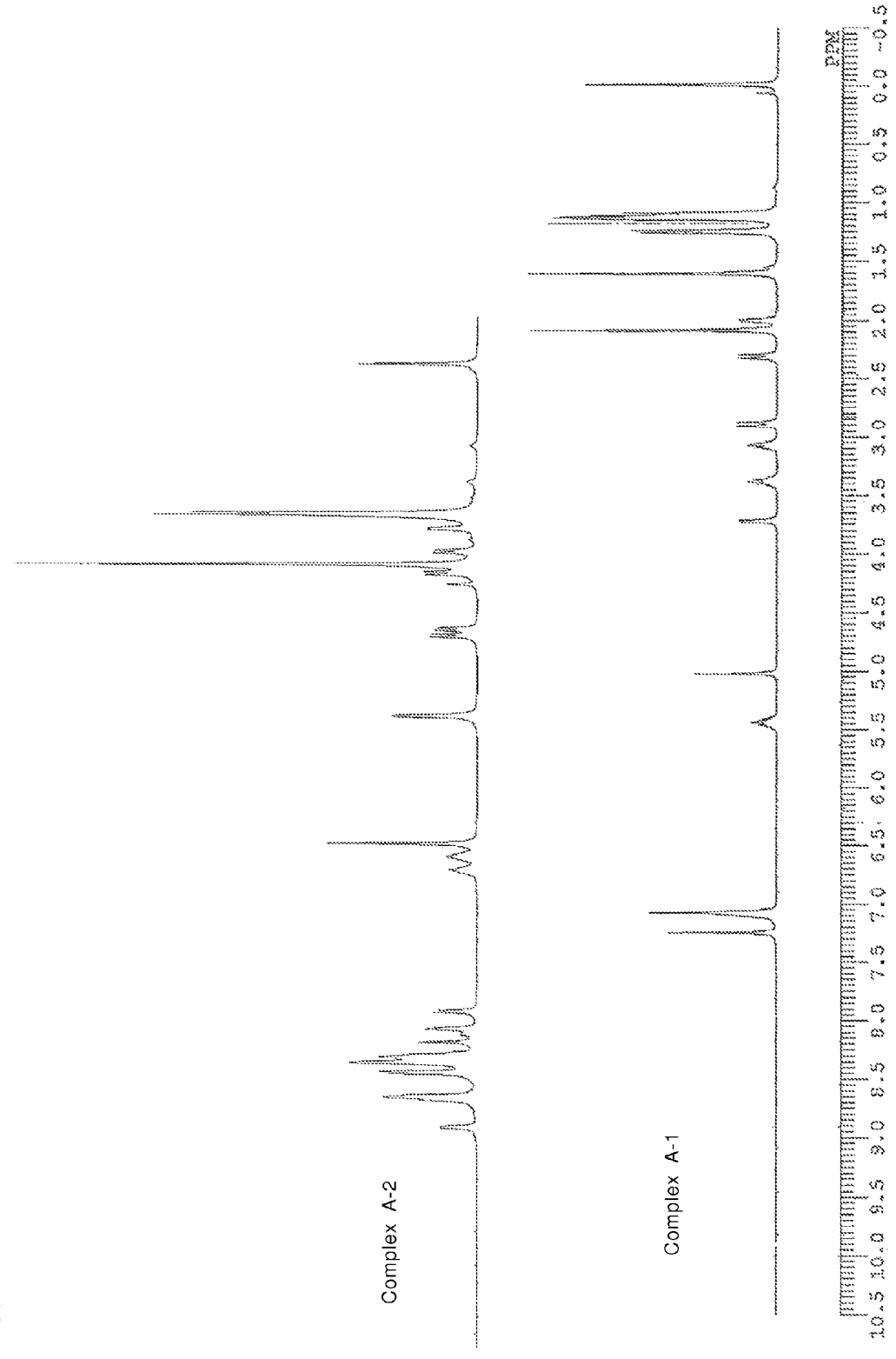
FIG. 1 is a $^1$H-NMR spectrum of the complex obtained in Examples 1 to 2.

Hereinafter, the present invention is described in greater detail.

[Catalyst for Polymerization of Norbornene Monomers]

The catalyst for the polymerization of norbornene monomers of the present invention comprises transition metal complex (A) as an essential component and cocatalyst (B) as being an ionic compound which can generate a cationic transition metal compound by reacting with transition metal complex (A) (hereinafter may be abbreviated as "cocatalyst (B)") and a phosphine ligand (C) as an optional component.

Transition Metal Complex (A)

The transition metal complex (A) as a component of the catalyst for polymerizing norbornene monomers of the present invention is characterized in comprising a transition metal having π-allyl ligand selected from the elements belonging to eight, nine or ten group of the periodic table for 1991 and β-ketoimine as being a bidentate ligand.

The transition metal complex (A) is represented by formula (1).

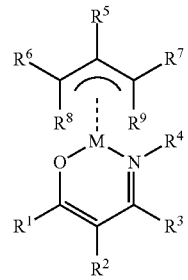

M in formula (1) represents one transition metal selected from the elements belonging to eight, nine or ten group of the periodic table for 1991. Specific examples include iron (Fe), cobalt (Co), nickel (Ni), ruthenium (Ru), rhodium (Rh), palladium (Pd) and platinum (Pt). Among these, preferred elements are cobalt, nickel, palladium and platinum from the viewpoint of the stability of the complex and ease of synthesis, and using nickel or palladium is more preferable.

$R^1$, $R^2$ and $R^3$ in formula (1) independently represent a hydrogen atom or a hydrocarbon group having 1 to 20 carbon atoms.

Specific examples of the hydrocarbon group having 1 to 20 carbon atoms include an alkyl group having 1 to 20 carbon atoms, which contains a linear or branched chain, such as a methyl group, ethyl group, n-propyl group, isopropyl group, n-butyl group, t-butyl group, isobutyl group, octyl group, 2-ethylhexyl group and 2-methoxyethyl group; a cycloalkyl group having 3 to 20 carbon atoms, such as a cyclopentyl group, cyclohexyl group, 4-methylcyclohexyl group and adamantyl group; an aryl group, an alkylaryl group or an aralkyl group having 6 to 20 carbon atoms such as a phenyl group, 1-naphthyl group, 2-methyl-1-naphthyl group, anthracenyl group, tolyl group, xylyl group and benzyl group. Among these, preferred are a hydrogen atom, an alkyl group having 1 to 6 carbon atoms and an aryl group having 6 to 20 carbon atoms from the viewpoint of ease of synthesizing a complex, and a hydrogen atom and an alkyl group having 1 to 4 carbon atoms are more preferable.

$R^4$ in formula (1) represents a hydrocarbon group having 1 to 20 carbon atoms. Specific examples include an alkyl group having 1 to 20 carbon atoms, which contains a linear or branched chain, such as a methyl group, ethyl group, n-propyl group, isopropyl group, n-butyl group, t-butyl group, isobutyl group, octyl group and 2-ethylhexyl group; a cycloalkyl group having 3 to 20 carbon atoms such as a cyclopentyl group, cyclohexyl group and 4-methylcyclohexyl group; and an aryl group, an alkylaryl group or an aralkyl group having 6 to 20 carbon atoms such as a phenyl group, tolyl group, xylyl group, 2,6-diisopropylphenyl group, 1-naphthyl group and benzyl group. Among these, preferred are an aryl group and alkylaryl group having 6 to 20 carbon atoms from the viewpoint of ease of synthesizing a complex and stability of the complex, and 1-naphthyl group and 2,6-diisopropylphenyl group are particularly preferable.

$R^5$, $R^6$, $R^7$, $R^8$ and $R^9$ in formula (1) independently represent a hydrogen atom, a halogen atom or a hydrocarbon group having 1 to 20 carbon atoms, and $R^5$, $R^6$, $R^7$, $R^8$ and $R^9$ may form a ring structure by bonding to each other. Specific examples include a hydrogen atom; a halogen atom such as a fluorine atom, chlorine atom and bromine atom; an alkyl group having 1 to 20 carbon atoms, which contains a linear or branched chain, such as a methyl group, ethyl group, n-propyl group, isopropyl group, n-butyl group, t-butyl group, isobutyl group, octyl group and 2-ethylhexyl group; an alkenyl group having 2 to 20 carbon atoms, which contains a linear or branched chain, such as an ethenyl group and 2-propenyl group; and an aryl group, an alkylaryl group or aralkyl group having 6 to 20 carbon atoms such as a phenyl group, tolyl group and xylyl group. Among these, preferred are a hydrogen atom, an alkyl group having 1 to 6 carbon atoms and an aryl group having 6 to 10 carbon atoms from the viewpoint of ease of synthesizing a complex, and a hydrogen atom and a methyl group are particularly preferable.

Specific examples of the transition metal complex (A) represented by formula (1) are given below but the transition metal complex (A) is not limited thereto. In the specific examples described below, "M" has the same meaning as "M" in formula (1). Also, Me, Et, t-Bu and Ph respectively represent a methyl group, an ethyl group, a t-butyl group and a phenyl group. In the specific examples, palladium or nickel is the most preferable as "M".

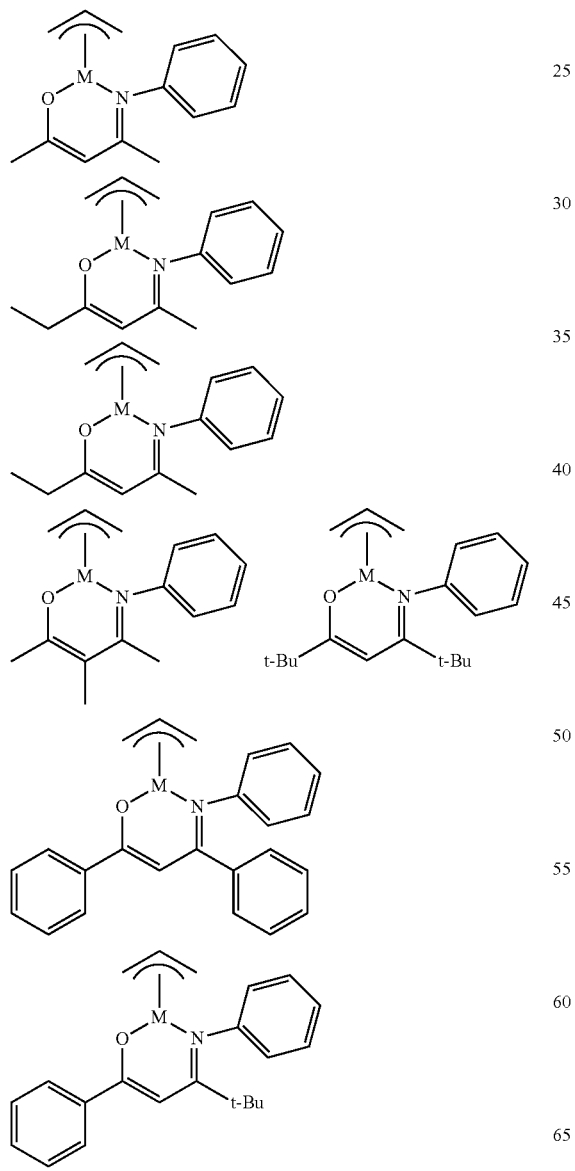
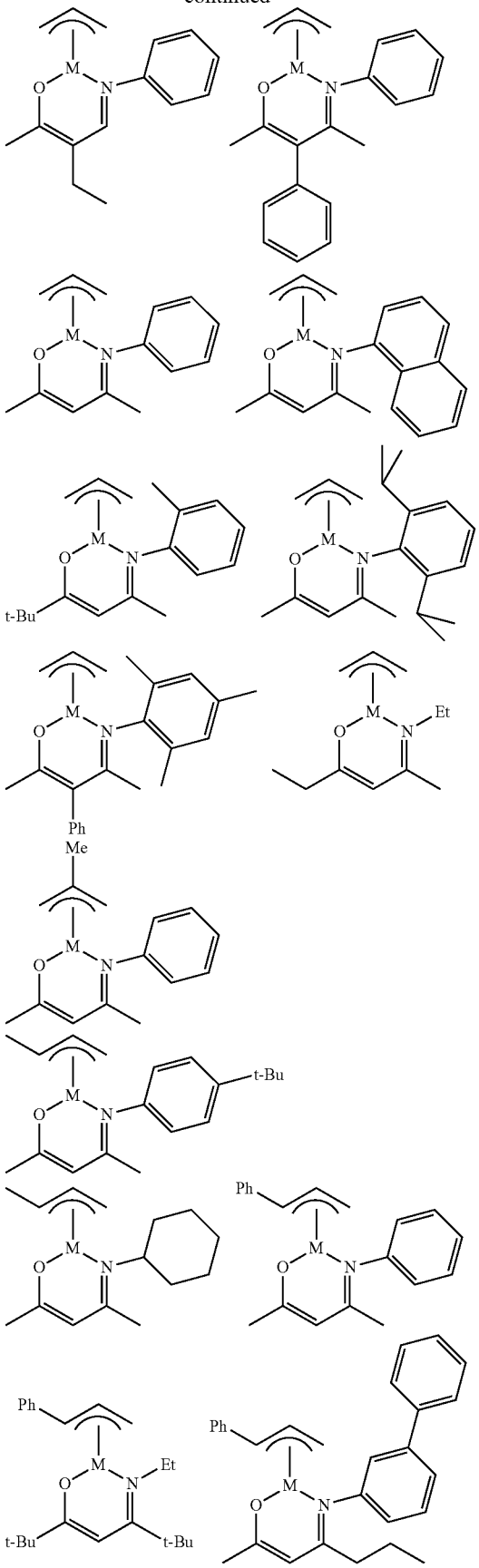

-continued

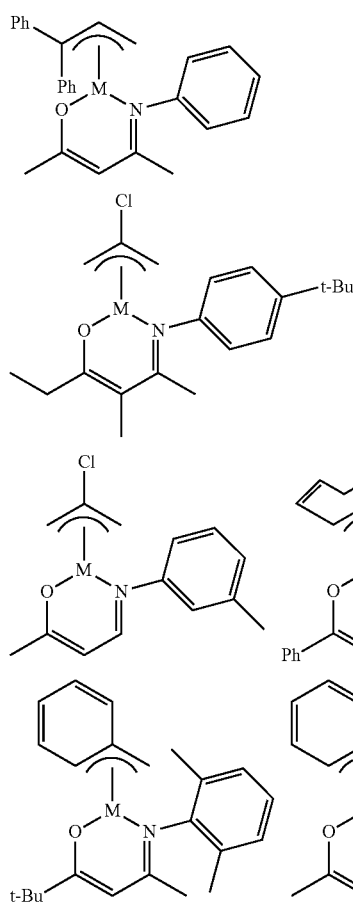

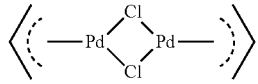

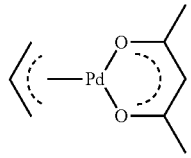

As a β-ketoimine compound used for production of transition metal complex (A), a β-ketoimine compound having $R^1$, $R^2$, $R^3$ and $R^4$ which correspond to the target transition metal complex (A) can be chosen. Specific examples of a β-ketoimine compound used for producing transition metal complex (A) are given below but the β-ketoimine compound is not limited thereto.

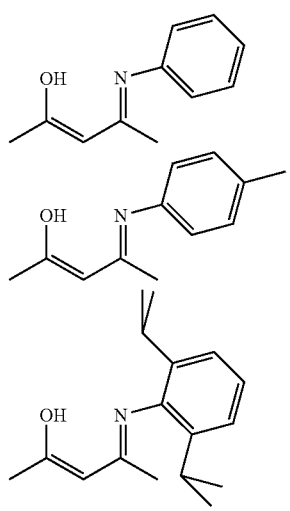

Among these, (π-allyl){4-(2,6-diisopropylphenylimino)-2-penten-2-olato-$\kappa^2$N,O}palladium, (π-allyl){4-(1-naphthylimino)-2-penten-2-olato-$\kappa^2$N,O}palladium are preferable.

The transition metal complex (A) of the present invention can be produced by the ligand exchange reaction of a (π-allyl)palladium(II) compound as a precursor and a β-ketoimine compound.

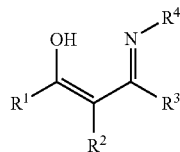

$R^1$, $R^2$, $R^3$ and $R^4$ in the formula have the same meanings as in formula (1). An example of the specific production method can be exemplified by the method disclosed by J. Organomet. Chem., 1973, 50, 333-348.

There is no particular limitation on a (π-allyl)palladium(II) compound as long as the compound contains a ligand capable of carrying out a ligand exchange reaction with a β-ketoimine compound. Compounds having $R^5$, $R^6$, $R^7$, $R^8$ and $R^9$ which correspond to the target transition metal complex (A) can be chosen. For example, di(π-allyl)di(p-chloro)dipalladium (formula (5)) and (π-allyl)(acetylacetonato)palladium (formula (6)) are preferable.

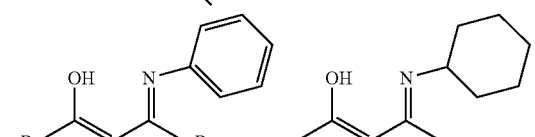

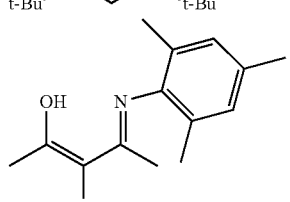

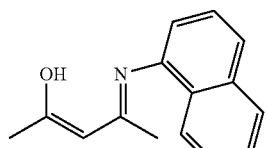

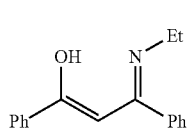

For such a β-ketoimine compound, commercially available ones can be used as they are. A compound produced by the method described by Organometallics, 2008, 27, 1671-1674 can also be used.

The above-mentioned ligand exchange reaction can be performed by adding a β-ketoimine compound or a β-ketoimine compound with base added as needed to a (π-allyl)palladium (II) compound as a precursor dissolved in a solvent followed by stirring at a predetermined temperature for a predetermined time.

There is no particular limitation on a solvent used in the ligand exchange reaction as long as the solvent is not reactive with each substrate, and examples include aliphatic hydrocarbon such as pentane, hexane and heptane; alicyclic hydrocarbon such as cyclohexane; aromatic hydrocarbon such as benzene, toluene and xylene; halogenated hydrocarbon such as dichloromethane, chloroform and chlorobenzene; nitrogen-containing hydrocarbon such as nitromethane, nitrobenzene and acetonitrile; and ether such as diethyl ether, dioxane and tetrahydrofuran. Two or more of these solvents may be used in mixture. It is preferable to use a solvent subjected to dehydration and deaeration.

There is no particular limitation on the usage of a solvent as long as it does not significantly delay the reaction, and the usage can be appropriately determined depending on the solubility of the (π-allyl)palladium(II) compound as a precursor and the like. Generally, 1 to 100 g of a solvent is used based on 1 g of (π-allyl)palladium(II) compound as a precursor.

There is no particular limitation on the polymerization temperature but the temperature is generally from −100° C. to 150° C., preferably from −50° C. to 120° C. If the temperature is lower than −100° C., it lowers the reaction rate. If the temperature is higher than 150° C., it results in decomposition of the generated complex in some cases. The reaction rate can be controlled by selecting the reaction temperature within the above-mentioned range.

The reaction time is not particularly limited and, for example, from one minute to 50 hours, preferably from 30 minutes to three hours, depending on the reaction temperature. Also, it is preferable to conduct reaction under inert gas atmosphere such as nitrogen or argon gas.

After the completion of the reaction, the target transition metal complex (A) can be isolated by performing general isolation/purification operation. Specifically, in the case where di(π-allyl)di(μ-chloro)dipalladium is used as a material, the target transition metal complex (A) is isolated by removing the salt generated in the reaction such as LiCl by centrifugation and filtration followed by recrystallization of the salt. Meanwhile, when (π-allyl)(acetylacetonato)palladium is used as a material, the target transition metal complex (A) is isolated by removing acetylacetone generated in the reaction by distilling away with solvent under reduced pressure followed by addition of a solvent and recrystallization of the salt.

Whether the product obtained by the reaction is the target transition metal complex (A) can be confirmed by NMR spectrum, element analysis, mass spectrum, X-ray crystallographic analysis and the like.

The thus obtained transition metal complex (A) is useful as a catalyst component for the polymerization of norbornene monomers.

While the catalyst for the polymerization of norbornene monomers of the present invention may be a compound comprising at least one member of transition metal complex (A), it is preferable that the catalyst further contains cocatalyst (B) as being an ionic compound, which can generate a cationic transition metal compound by reacting with transition metal complex (A), and a phosphine ligand (C), which enables exhibition of enhanced catalyst activity.

Cocatalyst (B)

Examples of cocatalyst (B) capable of producing a cationic transition metal compound through the reaction with the transition metal complex (A) used in the present invention include an ionic compound combining non-coordinating anions and cations.

Examples of non-coordinating anions include quaternary anions of the Group 13 element in the periodic table for 1991. Specific examples include tetra(phenyl)borate, tetra(fluorophenyl)borate, tetrakis(difluorophenyl)borate, tetrakis(trifluorophenyl)borate, tetrakis(tetrafluorophenyl)borate, tetrakis(pentafluorophenyl)borate, tetrakis(tetrafluoromethyl phenyl)borate, tetrakis[3,5-di(trifluoromethyl)phenyl]borate, tetra(tolyl)borate, tetra(xylyl)borate, triphenyl(pentafluorophenyl)borate, [tris(pentafluorophenyl)phenyl]borate and tridecahydride-7,8-dicarbaundeca-borate.

Examples of the above-mentioned cation include carbonium cation, oxonium cation, ammonium cation, phosphonium cation, cycloheptyltrienyl cation and ferrocenium cation having transition metal.

Specific examples of the carbonium cation include trisubstituted carbonium cation such as triphenylcarbonium cation and trisubstituted phenylcarbonium cation. Specific examples of trisubstituted phenylcarbonium cation include tri(methylphenyl)carbonium cation and tri(dimethylphenyl) carbonium cation.

Specific examples of the oxonium cation include alkyloxonium cation such as hydroxonium cation and methyloxonium cation, dialkyloxonium cation such as dimethyloxonium cation, and trialkyloxonium cation such as trimethyloxonium cation and triethyloxonium cation.

Specific examples of the ammonium cation include trialkylammonium cation such as trimethylammonium cation, triethylammonium cation, tripropylammonium cation, tri(n-butyl)ammonium cation; N,N-dialkylanilinium cation such as N,N-diethylanilinium cation and N,N-2,4,6-pentamethylanilinium cation; and dialkylammonium cation such as di(isopropyl)ammonium cation and dicyclohexylammonium cation.

Specific examples of the phosphonium cation include triarylphosphonium cation such as triphenylphosphonium cation, tri(methylphenyl)phosphonium cation and tri(dimethylphenyl)phosphonium cation.

Specific examples of the ferrocenium cation include dialkylferrocenium cation such as ferrocenium cation, 1,1-dimethylferrocenium cation and 1,1-diethylferrocenium cation.

Preferred examples of cocatalyst (B) are trityl tetrakis(pentafluorophenyl)borate, triphenylcarbonium tetra(fluorophenyl)borate, N,N-dimethylanilinium tetrakis(pentafluorophenyl)borate, trityl tetrakis[3,5-di(trifluoromethyl)phenyl] borate, N,N-dimethylanilinium tetrakis[3,5-di(trifluoromethyl)phenyl]borate and 1,1'-dimethylferrocenium tetrakis(pentafluorophenyl)borate.

Phosphine Ligand (C)

Phosphine ligand (C) used in the present invention is a trivalent phosphorus compound composed of three substituents selected independently from a hydrogen atom, an alkyl group or an aryl group. Specific examples include trialkylphosphine such as trimethylphosphine, triethylphosphine, triisopropylphosphine and tri-t-butylphosphine; and tricycloalkylphosphine such as tricyclopentylphosphine, tricyclohexylphosphine; and triarylphosphine such as triphenylphosphine. Among these, trialkylphosphine is preferable and triisopropylphosphine is particularly preferable from the viewpoint of enhancing the catalytic activity.

In the present invention, a catalyst using a complex represented by formula (1) as transition metal complex (A), wherein $R^1$, $R^2$, $R^3$ and $R^4$ represent a methyl group, a hydrogen atom, a methyl group and an aryl group, respectively, and all of $R^5$, $R^6$, $R^7$, $R^8$ and $R^9$ represent a hydrogen atom; N,N-dimethylanilinium tetrakis(pentafluorophenyl)borate $\{[C_6H_5]N(Me)_2H][B(C_6F_5)_4]\}$ or trityl tetrakis(pentafluorophenyl)borate $\{[(C_6H_5)_3C][B(C_6F_5)_4]\}$ as cocatalyst (B); and triisopropylphosphine as phosphine ligand (C) is a preferable embodiment of the catalyst capable of producing norbornene polymers with high catalytic activity.

Also, a catalyst using a complex represented by formula (1) as transition metal complex (A), wherein $R^1$ represents a methyl group, $R^2$ represents a hydrogen atom, $R^3$ represents a methyl group, and $R^4$ represents a 2,6-diisopropylphenyl group or a 1-naphthyl group and all of $R^5$, $R^6$, $R^7$, $R^8$ and $R^9$ represent a hydrogen atom; N,N-dimethylanilinium tetrakis (pentafluorophenyl)borate $\{[C_6H_5N(Me)_2H][B(C_6F_5)_4]\}$ as cocatalyst (B); and triisopropylphosphine as phosphine ligand (C) is the most preferable embodiment of the catalyst capable of producing norbornene polymers with high catalytic activity.

The use ratio of transition metal complex (A) and cocatalyst (B) in the method of the present invention varies depending on conditions and cannot be uniformly defined, however, the ratio of (A)/(B) (molar ratio) is generally from 1/0.1 to 1/100, preferably from 1/0.5 to 1/50, still more preferably from 1/1 to 1/10.

The use ratio of transition metal complex (A) and phosphine ligand (C) in the method of the present invention varies depending on conditions and cannot be uniformly defined, however, the ratio of (A)/(C) (molar ratio) is generally from 1/0.1 to 1/2, preferably from 1/0.5 to 1/1.8, still more preferably from 1/1 to 1/1.5.

There is no particular limitation on the temperature at which the catalyst components are placed in contact with each other but the temperature is generally from −100° C. to 150° C., preferably from −50° C. to 120° C. If the temperature is lower than −100° C., it lowers the reaction rate between each other of the components. If the temperature is higher than 150° C., it incurs decomposition of each of the components, thereby lowering the catalytic activity. By selecting the contact temperature within the above-mentioned range, the polymerization rate, the molecular weight of the generated polymer and the like can be controlled when the catalyst is used for polymerization.

Each of the catalyst components may be mixed in the presence of a solvent. Though there is no particular limitation on a solvent which can be used, preferred are those which do not have reactivity with each of the catalyst components and are produced at an industrial scale and easily-available. Specific examples of a solvent include aliphatic hydrocarbon such as pentane, hexane and heptane; alicyclic hydrocarbon such as cyclohexane; aromatic hydrocarbon such as benzene, toluene and xylene; halogenated hydrocarbon such as dichloromethane, chloroform and chlorobenzene; nitrogen-containing hydrocarbon such as nitromethane, nitrobenzene and acetonitrile; and ether such as diethylether, dioxane and tetrahydrofurane. Among these, aliphatic hydrocarbon, aromatic hydrocarbon and halogenated hydrocarbon are preferable. Two or more of these solvents may be used in mixture.

[Method for Producing Norbornene Polymers]

The method for producing norbornene polymers of the present invention is characterized in addition polymerization of norbornene monomers in the presence of the catalyst for the polymerization of the present invention.

The production method of the present invention is one of the following methods: i.e. (i) a method of obtaining addition homopolymers of norbornene monomers by the addition polymerization of one type of norbornene monomer alone, (ii) a method of obtaining addition copolymers of norbornene monomers by the addition copolymerization of two or more types of norbornene monomers, and (iii) a method of obtaining addition copolymers of norbornene monomers by the addition copolymerization of one or more types of norbornene monomers and one or more types of other vinyl monomers which is copolymerizable with norbornene monomers.

Norbornene Monomers

There is no particular limitation on the norbornene monomer used in the present invention as long as it is a compound containing a norbornene ring structure (hereinafter may be simply referred to as "norbornenes"). The compound may contain a polar or nonpolar substituent and may contain a ring structure other than a norbornene ring.

As norbornenes, compounds represented by formula (4) are preferable.

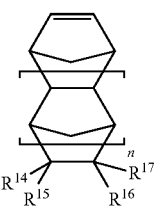

(4)

In the formula, $R^{14}$ to $R^{17}$ each independently represents a hydrogen atom; a halogen atom; a functional group containing a nitrogen atom, an oxygen atom, a sulfur atom, a halogen atom or a silicon atom; and a hydrocarbon group having 1 to 20 carbon atoms which may contain a halogen atom or the above-mentioned functional group. Also, $R^{14}$ to $R^{17}$ may bond to each other to form a ring. n is 0 or 1.

Norbornenes represented by formula (4) can be classified into bicyclo[2.2.1]hept-2-enes in which n is 0 and tetracyclo[6.2.1$^{3,6}$.0$^{2,7}$]dodec-4-enes in which n is 1. Either of them may be used in the production method of the present invention.

Specific examples of $R^{14}$ to $R^{17}$ in formula (4) include a hydrogen atom; a halogen atom such as a chlorine atom, a bromine atom and a fluorine atom; a functional group containing an oxygen atom such as hydroxyl group, alkoxy group, aryloxy group, carbonyl group, hydroxycarbonyl group, alkoxycarbonyl group and aryloxycarbonyl group; a functional group containing a nitrogen atom such as amino group, alkylamino group, arylamino group, aminocarbonyl group, alkylaminocarbonyl group, arylaminocarbonyl group and cyano group; a functional group containing a sulfur atom such as mercapto group, alkoxythio group and aryloxytio group; and a functional group containing a silicon atom such as silyl group, alkylsilyl group, arylsilyl group, alkoxysilyl group and aryloxysilyl group. Examples also include a hydrocarbon group having 1 to 20 carbon atoms such as alkyl group, alkenyl group and aryl group which may contain these functional groups. Furthermore, $R^{14}$ to $R^{17}$ may bond to each other to form a ring and examples of such a case include an acid anhydride structure, carbonate structure and dithiocarbonate structure.

Specific examples of norbornenes used in the present invention include bicyclo[2.2.1]hept-2-enes, which are unsubstituted or have hydrocarbon group, such as 2-norbornene, 5-methyl-2-norbornene, 5-ethyl-2-norbornene, 5-n-butyl-2-norbornene, 5-n-hexyl-2-norbornene, 5-n-decyl-2-norbornene, 5-cyclohexyl-2-norbornene, 5-ethylidene-2-norbornene, 5-vinyl-2-norbornene, 5-phenyl-2-norbornene, 5-benzyl-2-norbornene, dicyclopentadiene, dihydrodicyclopentadiene, tetracyclo[9.2.1.0$^{2,10}$.0$^{3,8}$]tetradeca-3,5,7,12-tetraene, tetracyclo[10.2.1.0$^{2,11}$.0$^{4,9}$]pentadeca-4,6,8,13-tetraene;

tetracyclo[6.2.1.1$^{3,6}$.0$^{2,7}$]dodec-4-enes, which are unsubstituted or have hydrocarbon group, such as tetracyclo[6.2.1.1$^{3,6}$.0$^{2,7}$]dodec-4-ene, 9-methyltetracyclo[6.2.1.1$^{3,6}$.0$^{2,7}$]dodec-4-ene, 9-ethyltetracyclo[6.2.1.1$^{3,6}$.0$^{2,7}$]dodec-4-ene, 9-n-butyltetracyclo[6.2.1.1$^{3,6}$.0$^{2,7}$]dodec-4-ene, 9-cyclohexyltetracyclo[6.2.1.1$^{3,6}$.0$^{2,7}$]dodec-4-ene, 9-ethylidenetetracyclo[6.2.1.1$^{3,6}$.0$^{2,7}$]dodec-4-ene, 9-vinyltetracyclo[6.2.1.1$^{3,6}$.0$^{2,7}$]dodec-4-ene and 9-phenyltetracyclo[6.2.1.1$^{3,6}$.0$^{2,7}$]dodec-4-ene;

bicyclo[2.1.1]hept-2-enes having alkoxycarbonyl group such as methyl 5-norbornene-2-carboxylate, ethyl 5-norbornene-2-carboxylate, n-butyl 5-norbornene-2-carboxylate, methyl 2-methyl-5-norbornene-2-carboxylate, ethyl 2-methyl-5-norbornene-2-carboxylate, n-butyl 2-methyl-5-norbornene-2-carboxylate, methyl 5-norbornene-2,3-dicarboxylate and ethyl 5-norbornene-2,3-dicarboxylate; tetracyclo[6.2.1.1$^{3,6}$.0$^{2,7}$]dodec-9-enes having alkoxycarbonyl group such as methyl tetracyclo[6.2.1.1$^{3,6}$.0$^{2,7}$]dodec-9-ene-4-carboxylate, ethyl tetracyclo[6.2.1.1$^{3,6}$.0$^{2,7}$]dodec-9-ene-4-carboxylate, methyl 4-methyltetracyclo[6.2.1.1$^{3,6}$.0$^{2,7}$]dodec-9-ene-4-carboxylate, methyl tetracyclo[6.2.1.1$^{3,6}$.0$^{2,7}$]dodec-9-ene-4,5-dicarboxylate and ethyl tetracyclo[6.2.1.1$^{3,6}$.0$^{2,7}$]dodec-9-ene-4,5-dicarboxylate;

bicyclo[2.2.1]hept-2-enes having hydroxycarbonyl group such as 5-norbornene-2-carboxylic acid and 5-norbornene-2,3-dicarboxylic acid; tetracyclo[6.2.1.1$^{3,6}$.0$^{2,7}$]dodec-9-enes having hydroxycarbonyl group such as tetracyclo[6.2.1.1$^{3,6}$.0$^{2,7}$]dodec-9-ene-4-carboxylic acid and tetracyclo[6.2.1.1$^{3,6}$.0$^{2,7}$]dodec-9-ene-4,5-dicarboxylic acid;

bicyclo[2.2.1]hept-2-enes having hydroxyl group such as 2-hydroxy-5-norbornene, 2-hydroxymethyl-5-norbornene, 2,2-di(hydroxymethyl)-5-norbornene and 2,3-di(hydroxymethyl)-5-norbornene; tetracyclo[6.2.1.1$^{3,6}$.0$^{2,7}$]dodec-9-enes having hydroxyl group such as tetracyclo[6.2.1.1$^{3,6}$.0$^{2,7}$]dodec-9-ene-4-ol, tetracyclo[6.2.1.1$^{3,6}$.0$^{2,7}$]dodec-9-ene-4-methanol and tetracyclo[6.2.1.1$^{3,6}$.0$^{2,7}$]dodec-9-ene-4,5-dimethanol;

bicyclo[2.2.1]hept-2-enes having acetoxyl group such as 2-acetoxy-5-norbornene, 2-acetoxymethyl-5-norbornene, 2,2-di(acetoxymethyl)-5-norbornene and 2,3-di(acetoxymethyl)-5-norbornene; tetracyclo[6.2.1.1$^{3,6}$.0$^{2,7}$]dodec-9-enes having acetoxyl group such as 4-acetoxytetracyclo[6.2.1.1$^{3,6}$.0$^{2,7}$]dodec-9-ene, 4-acetoxymethyltetracyclo[6.2.1.1$^{3,6}$.0$^{2,7}$]dodec-9-ene, and 4,5-di(acetoxymethyl)tetracyclo[6.2.1.1$^{3,6}$.0$^{2,7}$]dodec-9-ene;

bicyclo[2.2.1]hept-2-enes having a functional group containing a nitrogen atom such as 5-norbornene-2-carbonitrile and 5-norbornene-2-carboxamide; tetracyclo[6.2.1.1$^{3,6}$.0$^{2,7}$]dodec-9-enes having a functional group containing a nitrogen atom such as tetracyclo[6.2.1.1$^{3,6}$.0$^{2,7}$]dodec-9-ene-4-carbonitrile and tetracyclo[6.2.1.1$^{3,6}$.0$^{2,7}$]dodec-9-ene-4-carboxamide;

bicyclo[2.2.1]hept-2-enes having a halogen atom such as 2-chloro-5-norbornene and 2-fluoro-5-norbornene; tetracyclo[6.2.1.1$^{3,6}$.0$^{2,7}$]dodec-9-enes having a halogen atom such as 4-chlorotetracyclo[6.2.1.1$^{3,6}$.0$^{2,7}$]dodec-9-ene and 4-fluorotetracyclo[6.2.1.1$^{3,6}$.0$^{2,7}$]dodec-9-ene;

bicyclo[2.2.1]hept-2-enes having a functional group containing a silicon atom such as 2-trimethylsiloxy-5-norbornene, 2-trimethoxysilyl-5-norbornene and 2-tris(trimethoxysilyloxy)silyl-5-norbornene; tetracyclo[6.2.1.1$^{3,6}$.0$^{2,7}$]dodec-9-enes having a functional group containing a silicon atom such as 4-trimethylsiloxytetracyclo[6.2.1.1$^{3,6}$.0$^{2,7}$]dodec-9-ene, 4-trimethoxylsilyltetracyclo[6.2.1.1$^{3,6}$.0$^{2,7}$]dodec-9-ene, 4-tris(trimethoxylsilyloxy)tetracyclo[6.2.1.1$^{3,6}$.0$^{2,7}$]dodec-9-ene, bicyclo[2.2.1]hept-2-enes having an acid anhydride structure, a carbonate structure and a dithiocarbonate structure such as 5-norbornene-2,3-dicarboxylic acid anhydride, 5-norbornene-2,3-carbonate and 5-norbornene-2,3-dithiocarbonate; and tetracyclo[6.2.1.1$^{3,6}$.0$^{2,7}$]dodec-9-enes having an acid anhydride structure, a carbonate structure and a dithiocarbonate structure such as tetracyclo[6.2.1.1$^{3,6}$.0$^{2,7}$]dodec-9-ene-4,5-dicarboxylic acid anhydride, tetracyclo[6.2.1.1$^{3,6}$.0$^{2,7}$]dodec-9-ene-4,5-carbonate and tetracyclo[6.2.1.1$^{3,6}$.0$^{2,7}$]dodec-9-ene-4,5-dithiocarbonate.

These norbornenes may be used singly or in combination of two or more thereof.

Among these norbornenes, it is preferable to use norbornenes corresponding to the monomer unit represented by formulae (2) and (3) in the present invention

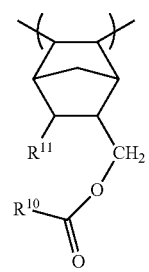

(2)

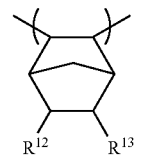

(3)

(in the formula, $R^{10}$ represents an alkyl group having 1 to 10 carbon atoms, and $R^{11}$, $R^{12}$ and $R^{13}$ each independently represent a hydrogen atom or an alkyl group having 1 to 10 carbon atoms).

Alkyl groups having 1 to 10 carbon atoms represented by $R^{10}$ in formula (2) may be linear or branched.

Examples of linear alkyl groups include methyl group, ethyl group, n-propyl group, n-butyl group, n-pentyl group, n-hexyl group, n-octyl group and n-decyl group.

Examples of branched alkyl groups include isopropyl group, isobutyl group, sec-butyl group, neo-pentyl group, isohexyl group, isooctyl group and isodecyl group.

Preferred among them is linear alkyl group having 1 to 3 carbon atoms from an economic standpoint. From the viewpoint of costs for producing a monomer, methyl group is particularly preferable.

$R^{11}$ in formula (2) and $R^{12}$ and $R^{13}$ in formula (3) independently represent for a hydrogen atom or alkyl group having 1 to 10 carbon atoms, and the alkyl group having 3 to 10 carbon atoms may be branched. Examples of these alkyl groups include those similar to the above-mentioned alkyl groups as $R^{10}$. Preferred among them is a hydrogen atom from the viewpoint of costs for producing a monomer.

Provided that $R^{11}$ is a hydrogen atom, the norbornene monomer as a material of the monomer unit represented by formula (2) is 2-acetoxymethyl-5-norbornene when $R^{10}$ is an alkyl group having one carbon atom, 2-[(ethylcarbonyloxy)methyl]-5-norbornene when $R^{10}$ is an alkyl group having two carbon atoms, and 2-[(propylcarbonyloxy)methyl]-5-norbornene when $R^{10}$ is a linear alkyl group having three carbon atoms.

Provided that $R^{12}$ and $R^{13}$ are hydrogen atoms, the norbornenes as a material of the monomer unit represented by formula (3) is norbornene.

In production method of the present invention, polymerization of a norbornene monomer using the above-mentioned transition metal complex (A), cocatalyst (B) and phosphine ligand (C) may be performed by bulk polymerization, suspension polymerization, emulsion polymerization, solution polymerization or precipitation polymerization. When the polymerization is performed in a solvent, it is necessary to use a solvent which will not adversely affect the catalyst activity. Examples of a solvent that can be used include aliphatic hydrocarbon such as pentane, hexane and heptane; alicyclic hydrocarbon such as cyclohexane; aromatic hydrocarbon such as benzene, toluene and xylene; halogenated hydrocarbon such as dichloromethane, chloroform and chlorobenzen; nitrogen-containing hydrocarbon such as nitromethane, nitrobenzene and acetonitrile; ether such as diethyl ether, dioxane and tetrahydrofurane; ester such as ethyl acetate, n-propyl acetate and n-butyl acetate; lactone such as δ-valerolactone and γ-butyrolactone; and water. Two or more of these solvents may be used in mixture. When water is used as a solvent, the reaction solution may be made in an emulsified state using anionic, cationic or nonionic surfactants and the like.

Precipitation polymerization is a kind of solvent polymerization, and a solvent capable of dissolving monomers but not capable of dissolving polymers is used. Since polymer is precipitated along with polymerization in the precipitation polymerization, it eliminates the needs of a poor solvent such as methanol used in large quantity for reprecipitation purification, which is advantageous in terms of the production cost. For the (co)polymer of the present invention, mixed solvent of toluene and ethyl acetate and the like is suitable for precipitation polymerization.

Main catalyst (A), cocatalyst (B) and phosphine ligand (C) are mixed when polymerization is performed. The order in which these are mixed is not particularly limited as long as main catalyst (A) is mixed with phosphine ligand (C) before (A) is placed in contact with cocatalyst (B). The component of main catalyst (A) and phosphine ligand (C) are mixed in advance and cocatalyst (B) is further added thereto to obtain a reaction composition and the composition may be added to a solution containing monomer to be polymerized. Also, cocatalyst (B) may be added to a solvent containing monomer to be polymerized, main catalyst (A) and phosphine ligand (C); or a mixture of main catalyst (A) and phosphine ligand (C) may be added to a mixture solution of monomer to be polymerized and cocatalyst (B).

In the present invention, it is preferable to mix main catalyst (A) and phosphine ligand (C) in advance to be in contact with each other for more than one minute, preferably for about 30 minutes to one hour and then mixed with cocatalyst (B) to be added to a reaction system containing cocatalyst (B); or to add a mixture of main catalyst (A) and phosphine ligand (C) to a reaction system containing cocatalyst (B). Such an operation enables exhibition of enhanced polymerization activity.

There is no particular limitation on the polymerization temperature but the temperature is generally from −100° C. to 150° C., preferably from −50° C. to 120° C. If the temperature is lower than −100° C., it lowers the polymerization rate. If the temperature is higher than 150° C., it lowers the catalytic activity in some cases. The polymerization rate and molecular weight can be controlled by selecting the polymerization temperature within the above-mentioned range.

The polymerization time is not particularly limited and, for example, from one minute to 100 hours. Also, it is preferable to conduct reaction under inert gas atmosphere such as nitrogen gas.

After the completion of the polymerization reaction, norbornene polymer as a reaction product can be subjected to post treatment by known operation and treating method (e.g. reprecipitation) and can be isolated through fractionation by filtration and subsequent drying.

In the norbornene copolymer composed of the monomer unit represented by formula (2) and formula (3) produced by the production method of the present invention, the content of the monomer unit represented by formula (2) is preferably 10 to 70 mol %. If the content of the monomer unit represented by formula (2) is less than 10 mol %, hydrophobicity of the copolymer increases, which decreases the solubility of the copolymer in the organic solvent while making the water absorption rate lower. On the other hand, if the content exceeds 70 mol %, the copolymer becomes hydrophilic, which increases the solubility of the copolymer in the organic solvent while making the water absorption rate higher. Accordingly, it is possible to control the solubility in the organic solvent and water absorption rate of the copolymer by adjusting the content of the monomer unit represented by formula (2).

In the norbornene copolymer composed of the monomer unit represented by formula (2) and formula (3) produced by the production method of the present invention, it is preferred that the content of the monomer unit represented by formula (2) be from 10 to 80 mol % in consideration for achieving a good balance between adequate solubility which is required when the norbornene copolymer of the present invention is formed into a film, a sheet and the like and low water absorption of the copolymer, more preferably 15 to 70 mol %, most preferably 20 to 60 mol %. The content of the monomer unit represented by formula (2) can be calculated from the integration value of $^1$H-NMR spectrum measured by dissolving the copolymer in powder form or film form in an appropriate deuterated solvent.

The norbornene (co)polymer produced by the production method of the present invention basically comprises norbornenes only. However, even so, it does not exclude the existence of a minute amount, e.g. 1 mol % or less, of the third monomer unit which would not affect the properties of the norbornene (co)polymer of the present invention. Also, the norbornene (co)polymer produced by the method of the present invention may be copolymerized with a third monomer without undermining the effect of the present invention in an effort to improve the properties.

There is no particular limitation on the third monomer, and preferred are monomers having an ethylenic carbon-carbon double bond. Examples are α-olefins such as ethylene, propylene, 1-butene, 1-pentene and 1-hexene; aromatic vinyl compounds such as styrene, α-methylstyrene and divinylbenzene; chain conjugated dienes such as 1,3-butadiene and isoprene; vinyl ethers such as ethylvinyl ether and propylvinyl ether; acrylates such as methyl acrylate, ethyl acrylate and 2-ethylhexyl acrylate; and methacrylate such as methyl methacrylate and ethyl methacrylate. Among these, α-olefins such as ethylene, propylene and 1-hexene; and aromatic vinyl compounds such as styrene are particularly preferable.

In the norbornene copolymer produced by the production method of the present invention, the bonding mode of each of the monomer units may be random, block or alternate, depending on polymerization conditions. In consideration for enhancement in mechanical properties of the copolymer, random mode is preferred.

The number average molecular weight (Mn) of the norbornene (co)polymer produced by the production method of the present invention of the present invention in terms of polystyrene measured by gel permeation chromatography (GPC) is preferably from 50,000 to 2,000,000, more preferably 100,000 to 1,500,000. If the number average molecular weight (Mn) in terms of polystyrene is less than 50,000, mechanical strength of the (co)polymer becomes insufficient. The number average molecular weight (Mn) in terms of polystyrene exceeding 2,000,000 not only lowers solvent solubility of the (co)polymer at the time of forming a cast film but also increases solution viscosity, which degrades molding workability of the (co)polymer. Also, the molecular weight distribution (Mw/Mn; weight average molecular weight/number average molecular weight) is preferably from 1.00 to 4.00, more preferably 1.30 to 3.50, still more preferably 1.50 to 3.00. If the (co)polymer has a wide molecular weight distribution range, the (co)polymer solution becomes less likely to be uniform at the time of forming a cast film, which makes it difficult to produce an excellent film.

Among the norbornene (co)polymers produced by the production method of the present invention, preferred is the polymer comprising the monomer units represented by formula (2) only

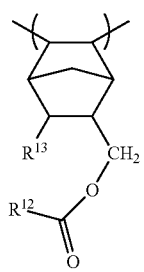

(2)

(symbols in the formula have the same meaning as mentioned above). The number average molecular weight (Mn) of the polymer is 200,000 to 1,000,000. When the number average molecular weight is less than 200,000, it lowers the chemical resistance while when the number average molecular weight exceeds 1,000,000, it not only decreases the solubility of the polymer in a solvent when forming a cast film but also increases the solution viscosity, to thereby lower the molding processability of the polymer.

The saturated water absorption of the norbornene (co)polymer produced by the method of the present invention at 23° C. is generally from 0.001 to 1 mass %, preferably from 0.005 to 0.7 mass %, still more preferably from 0.01 to 0.5 mass %. When the saturated water absorption of the (co)polymer is within the above-mentioned range, various optical properties such as transparency, phase difference, uniformity of phase difference and dimensional accuracy of the (co)polymer are maintained even under conditions of high temperature and humidity. Therefore the products are excellent in adhesion properties to the other materials and will not experience peel-off while in use. Also, since the (co)polymer has good compatibility with additives such as an antioxidant, the (co)polymer allows increasing addition degree of freedom. The above-mentioned saturated water absorption is determined by dipping the (co)polymer in water at 23° C. for 24 hours and measuring the increased mass according to the method described in JIS K7209.

The glass-transition temperature (Tg) of the norbornene (co)polymer produced by the method of the present invention may vary depending on the type of the monomer units which constitute the polymer, composition ratio (in the case where the polymer is a copolymer), and the presence or absence of the additives and the like, but is generally from 80 to 350° C., preferably from 100 to 320° C., still more preferably from 120 to 300° C. If Tg falls below the above-mentioned range, the heat distortion temperature becomes lower, which may cause a problem for heat resistance and optical properties of the obtained optical film may vary widely with temperature. If Tg is above the above-mentioned range, it increases the likelihood of heat deterioration of the (co)polymer resin when the (co)polymer is heated near to Tg during the stretching process.

The norbornene (co)polymer produced by the production method of the present invention can be processed into a film by the film formation according to a solution casting method. As a solvent to be used, toluene, tetrahydrofuran (THF), dichloromethane, chloroform and the like can be used.

EXAMPLES

Hereinafter, the present invention is described in more details by referring to Examples and Comparative Examples. The present invention is by no means limited thereto.

In each of Examples and Comparative Examples, the catalytic activity was determined by the following formula.

Catalytic activity=(the amount of the obtained polymer (g))/(amount by mole of palladium [mmol])  [Formula 1]

The weight average molecular weight (Mw), number average molecular weight (Mn) and molecular weight distribution (Mw/Mn) of the obtained polymer were determined by gel permeation chromatography (GPC) using polystyrene as a standard substance. The composition ratio of norbornene and 5-acetoxymethyl-2-norbornene (abbreviated as "ANB") in the copolymer was determined by the integration ratio of the peak in $^1$H-NMR spectra for "—COOCH$_2$—" unit of 5-acetoxymethyl-2-norbornene at δ:3.5-4.5 ppm; and peaks in $^1$H-NMR spectra for "CH$_3$COO—", "—CH$_2$—" and "—CH═" units of norbornene (abbreviated as "NB") and 5-aceoxymethyl-2-norbornene at δ:0.5-3.0 ppm. The ANB content rate was calculated by the following formula.

ANB content rate={(amount by mole of ANB units in the polymer)/(amount by mole of NB units in the polymer+amount by mole of ANB units in the polymer)}×100  [Formula 2]

Properties of the substances synthesized in Examples and Comparative Examples were measured as follows.

1. $^1$H-NMR, $^{13}$C-NMR
Apparatus used: JEOL EX-400
(400 MHz, manufactured by JEOL, LTD.)
Measurement method: measured by dissolving samples in deuterated chloroform and using tetramethylsilane as internal standard substance.

2. FT-IR
Apparatus used:
System: Spectrum GX (manufactured by PerkinElmer, Inc.)
ATR: MIRacle™ (manufactured by Pike Technologies)
Measurement method:
measured by a single reflection ATR method
3. Gel permeation chromatography (GPC)
Apparatus used:
Column: Shodex GPC K-G+KF-806L×2 (manufactured by SHOWA DENKO K.K.),
Detector: Shodex SE-61 (manufactured by SHOWA DENKO K.K.),
Measurement conditions
Solvent: tetrahydrofuran,
Measurement temperature: 40° C.,
Flow rate: 1.0 ml/minute,
Sample concentration: 1.0 mg/ml,
Injection amount: 1.0 µl,
Calibration curve: Universal Calibration curve,
Analysis program: SIC 48011 (product of System Instruments, Inc.)
4-(2,6-diisopropylphenylimino)pentan-2-one was synthesized according to the synthesis method of Rojas et al. (Organometallics, 2008, 27, 1671), and 4-(1-naphthylimino)pentan-2-one was synthesized according to synthesis method of Wang et al. (European Polymer Journal, 2006, 42, 322).

Synthesis Example 1

Synthesis of 2-acetoxymethyl-5-norbornene

Dicyclopentadiene (manufactured by Tokyo Chemical Industry Co., Ltd.; 759.80 g, 5.747 mol), allyl acetate (manufactured by Tokyo Chemical Industry Co., Ltd., 1,457.86 g, 14.561 mol) and hydroquinone (manufactured by Wako Pure Chemical Industries Co., Ltd., 2.25 g, 0.0204 mol) were placed in a 10 liter-volume stainless-steel made autoclave. After the inside of the reaction system was substituted with nitrogen gas, the autoclave was heated to 190° C. while stirring the content at 500 rpm, and reaction was carried out for five hours. After the completion of the reaction, the autoclave was cooled to room temperature and the content was transferred to the distillation equipment to be distilled under reduced pressure. As a fraction at 0.07 kPa and 48° C., 1,306.70 g of a clear colorless liquid substance was obtained.

The $^1$H-NMR spectrum of the obtained liquid substance was measured and it was confirmed that the substance was the target 2-acetoxymethyl-5-norbornene. The molar ratio of exo isomer and endo isomer (exo/endo) of the obtained 2-acetoxymethyl-5-norbornene was 18/82.

Example 1

Synthesis of (π-allyl){4-(2,6-diisopropylphenylimino)-2-penten-2-olato-κ$^2$N,O}palladium (Complex A-1)

[Complex A-1]

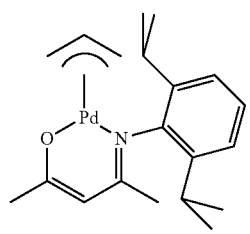

After the inside of a two-neck flask equipped with a three-way stopcock was substituted with nitrogen, 4-(2,6-diisopropylphenylimino)pentan-2-one (471.6 mg, 1.818 mmol) was added thereto and dissolved in anhydrous tetrahydrofuran (manufactured by Wako Pure Chemical Industries Co., Ltd.; 10 ml). After the resultant mixture was dipped in a dry ice-ethanol bath and cooled to −78° C., a solution of 1.6 mol n-butyllithium in 1 l of hexane (manufactured by Wako Pure Chemical Industries Co., Ltd.; 1.14 ml, 1.82 mmol) was delivered by drops into the mixture. After the instillation was completed, the mixture was stirred at −78° C. for one hour, and gradually restored to room temperature.

After the inside of a two-neck flask equipped with a three-way stopcock as separately prepared was substituted with nitrogen, allylpalladium chloride dimer (manufactured by Wako Pure Chemical Industries Co., Ltd.; 329.1 mg, 0.900 mmol) was charged into the flask and dissolved in anhydrous dichloromethane (manufactured by Wako Pure Chemical Industries Co., Ltd.; 20 ml).

Figure 2:
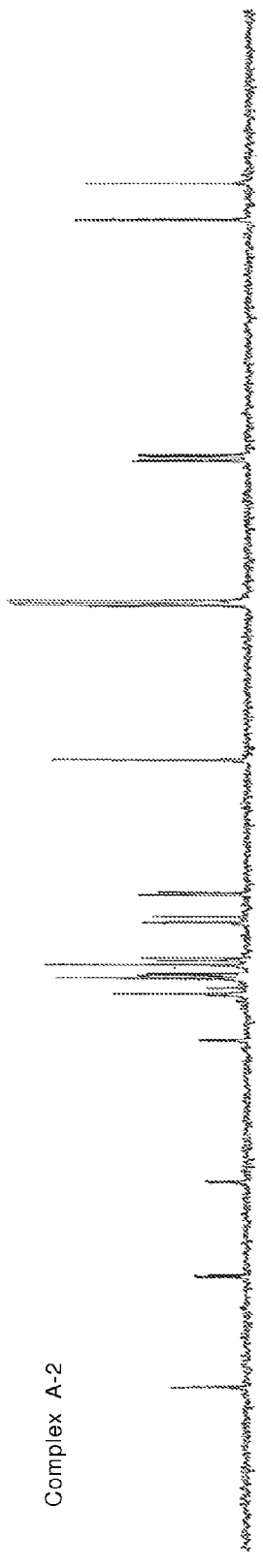
FIG. 2 is a $^{13}$C-NMR spectrum of the complex obtained in Examples 1 to 2.
Figure 2:
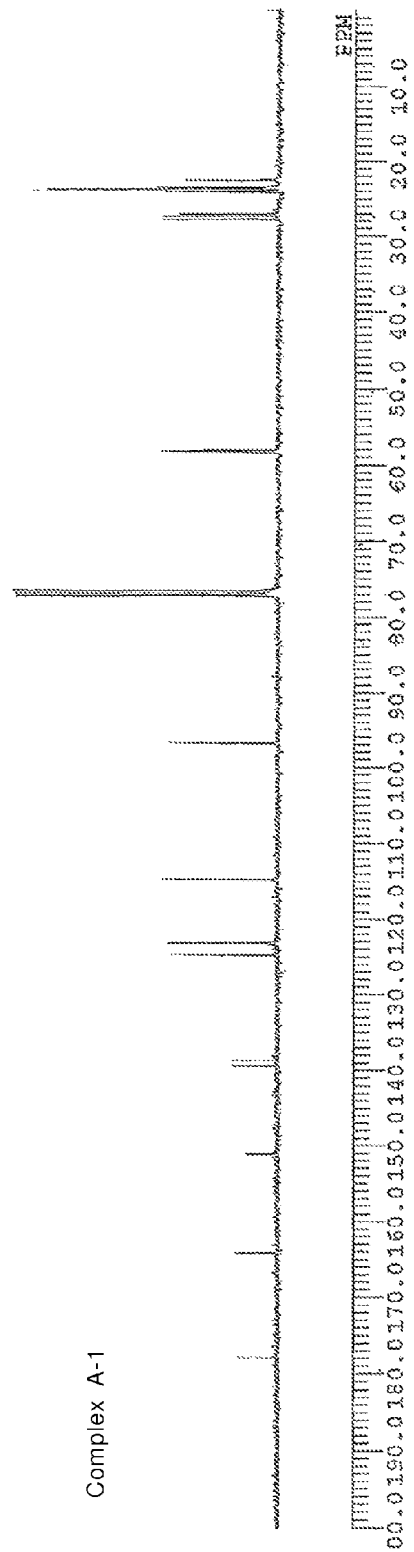

The solution was dipped in an ice bath to be cooled to 0° C. and a mixed solution of tetrahydrofuran/hexane prepared in advance was delivered slowly by drops for five minutes to carry out the reaction at 0° C. for one hour. After that, the solvent was completely distilled away under reduced pressure. After newly adding anhydrous toluene (manufactured by Wako Pure Chemical Industries Co., Ltd.; 20 ml) thereto followed by stirring, the solution was subjected to centrifugation under nitrogen atmosphere to thereby remove unnecessary salts and recover the supernatant toluene solution. The solution was condensed under reduced pressure followed by recrystallization from n-hexane to obtain 422 mg of brown crystals. The $^1$H-NMR, $^{13}$C-NMR and IR spectra of the obtained crystal were measured and it was confirmed that the crystal was (π-allyl){4-(2,6-diisopropylphenylimino)-2-penten-2-olato-κ$^2$N,O}palladium (Complex A-1). The $^1$H-NMR spectrum and $^{13}$C-NMR spectrum are shown in FIG. 1 and FIG. 2, respectively.

Example 2

Synthesis of (π-allyl){4-(1-naphthylimino)-2-penten-2-olato-κ$^2$N,O}palladium (Complex A-2)

[Complex A-2]

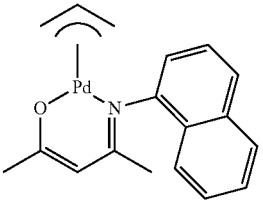

After the inside of a two-neck flask equipped with a three-way stopcock was substituted with nitrogen, 4-(1-naphthylimino)pentan-2-one (378.0 mg, 1.678 mmol) was added thereto and dissolved in anhydrous tetrahydrofuran (manufactured by Wako Pure Chemical Industries Co., Ltd.; 10 ml). After the resultant mixture was dipped in a dry ice-ethanol bath and cooled to −78° C., a solution of 1.6 mol n-butyllithium in 1 l of hexane (manufactured Wako Pure Chemical Industries Co., Ltd.; 1.14 ml, 1.82 mmol) was delivered by drops into the mixture. After the instillation was completed, the mixture was stirred at −78° C. for 20 minutes and then gradually restored to room temperature.

After the inside of a two-neck flask equipped with a three-way stopcock as separately prepared was substituted with nitrogen, allylpalladium chloride dimer (manufactured by Wako Pure Chemical Industries Co., Ltd.; 301.2 mg, 0.823 mmol) was charged into the flask and dissolved in anhydrous dichloromethane (manufactured by Wako Pure Chemical Industries Co., Ltd.; 10 ml).

The solution was dipped in a dry ice-ethanol bath to be cooled to −78° C. and into the solution a mixed solution of tetrahydrofuran/hexane prepared in advance was delivered slowly by drops for five minutes to carry out the reaction at −78° C. for one hour. Then the solvent was completely distilled away under reduced pressure. After newly adding anhydrous toluene (manufactured by Wako Pure Chemical Industries Co., Ltd.; 20 ml) thereto followed by stirring, the solution was subjected to centrifugation under nitrogen atmosphere to thereby remove unnecessary salts and recover the supernatant toluene solution. The solution was condensed under reduced pressure followed by recrystallization to obtain 144 mg of gray solid. The $^1$H-NMR, $^{13}$C-NMR and IR spectra of the obtained solid were measured and it was confirmed that the solid was (π-allyl){4-(1-naphthylimino)-2-penten-2-olato-$\kappa^2$N,O}palladium (Complex A-2). The $^1$H-NMR spectrum and $^{13}$C-NMR spectrum are shown in FIG. 1 and FIG. 2, respectively.

Example 3

Addition copolymerization of norbornene and 2-acetoxymethyl-5-norbornene

After the inside of a three-neck flask equipped with a three-way stopcock and a mechanical stirrer was substituted with nitrogen, norbornene (manufactured by Tokyo Chemical Industry Co., Ltd.; 4.71 g, 0.050 mol) and 2-acetoxymethyl-5-norbornene prepared in Synthesis Example 1 (16.62 g, 0.100 mol) were added thereto and dissolved in 75 ml of toluene. After further adding thereto a solution of N,N-dimethylanilinium tetrakis(pentafluorophenyl)borate [($C_6$HO$(CH_3)_2$NH][B$(C_6F_5)_4$] (manufactured by Tosoh Finechem Corporation, Inc.; 8.0 mg, 0.010 mmol) dissolved in 1 ml of dichloromethane, the resultant solution was heated to 70° C. A catalyst solution of (π-allyl){4-(2,6-diisopropylphenylimino)-2-penten-2-olato-$\kappa^2$N,O}palladium (Complex A-1) (4.1 mg, 0.010 mmol) synthesized in Example 1 and prepared in another vessel and triisopropyl phosphine [P(i-$C_3H_7)_3$] (manufactured by Strem Chemicals, Inc.; 1.6 mg, 0.010 mmol) dissolved in 3.5 ml of toluene was added to the reaction solution, thereby carrying out the polymerization reaction at 70° C. for 30 minutes. Subsequently, a solution of norbornene as prepared separately (Tokyo Chemical Industries Co., Ltd.; 4.71 g, 0.050 ml) dissolved in 5.4 ml of toluene was added to the reaction solution, and the polymerization reaction was carried out at 70° C. for another 30 minutes. After the reaction was completed, 8 ml of methanol added with small quantity of hydrochloric acid was added to the reaction solution to thereby terminate the reaction. Next, the reaction solution was diluted with toluene and put into large quantity of methanol to precipitate polymers. The precipitated polymer was separated by filtration followed by washing, and then dried at 90° C. under reduced pressure for five hours to obtain 8.73 g of polymer in the white powder form. The catalytic activity calculated based on the polymer yield and the charge of the catalyst was 873 g of polymer/mmol of palladium (Pd).

Figure 3:
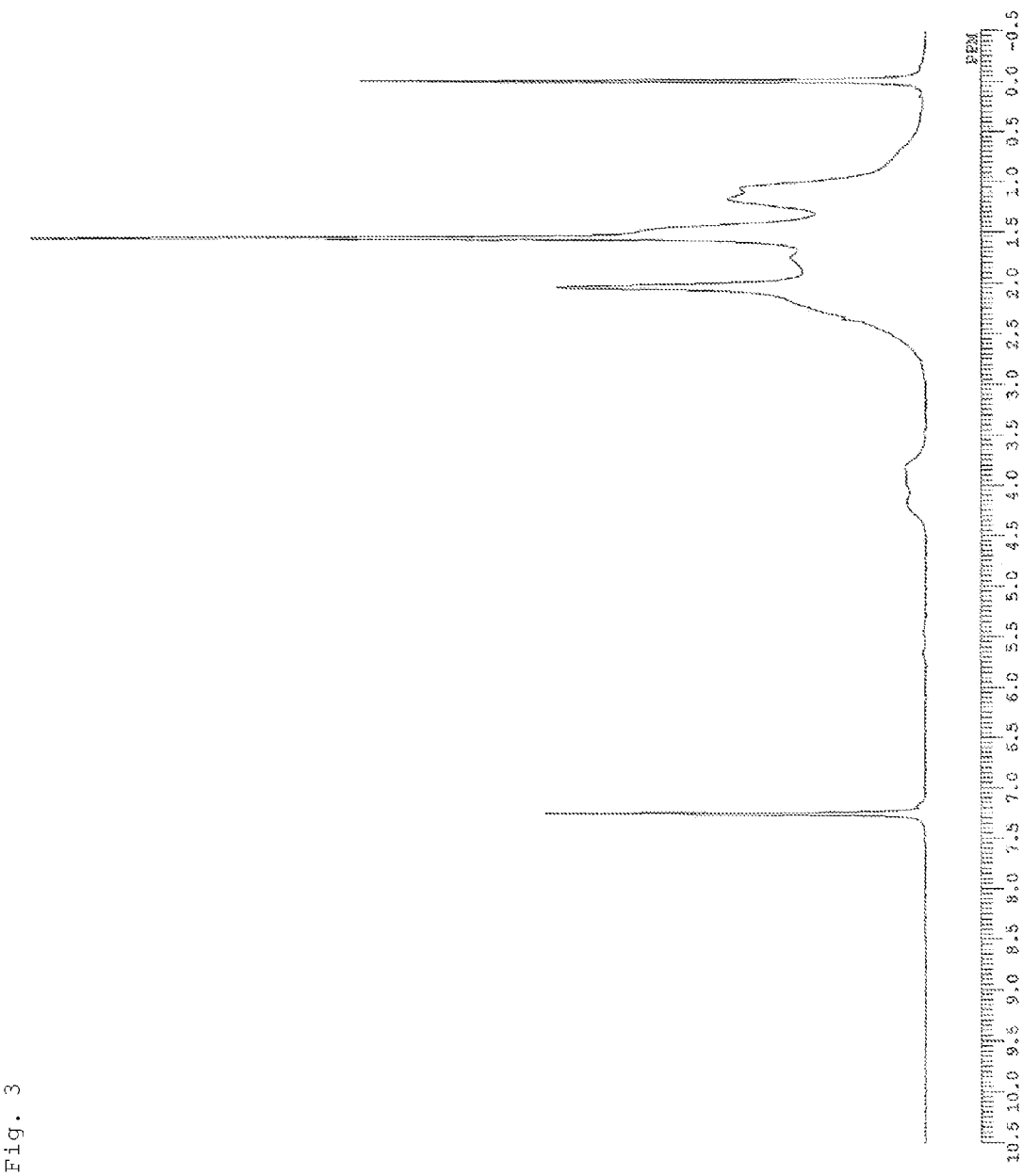
FIG. 3 is a $^1$H-NMR spectrum of the copolymer obtained in Example 3.
Figure 4:
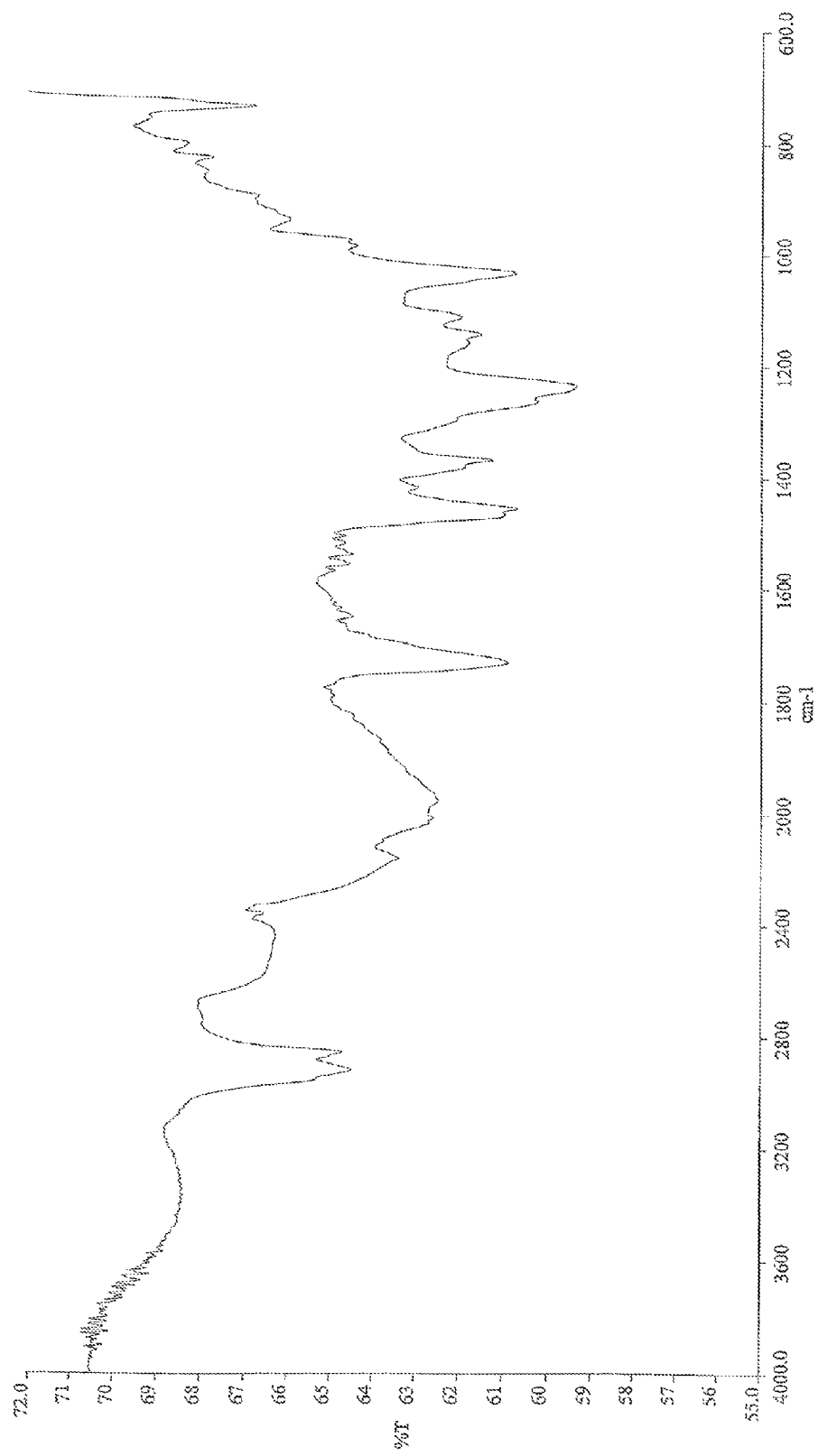
FIG. 4 is an IR spectrum of the copolymer obtained in Example 3.
Figure 5:
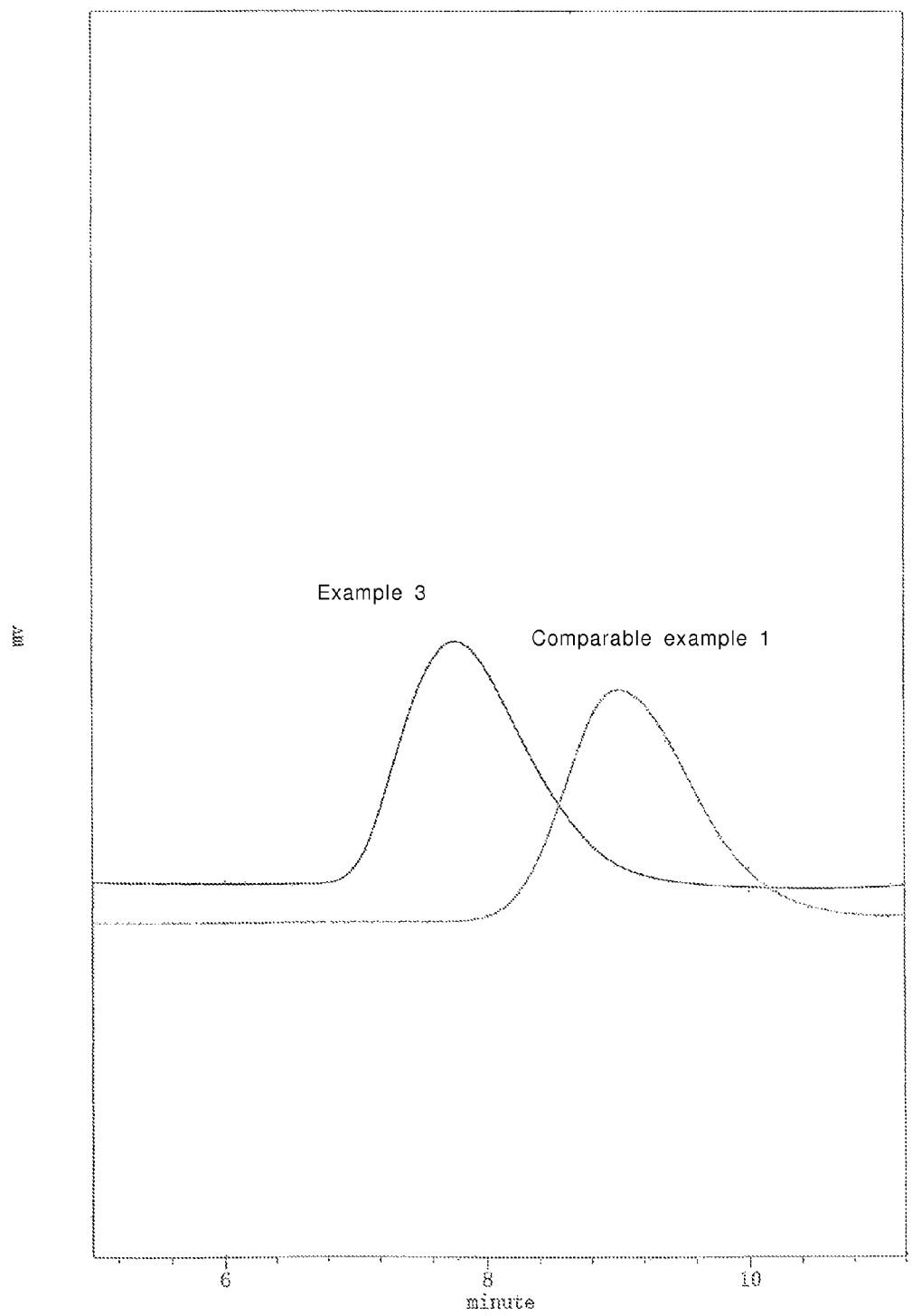
FIG. 5 is a gel permeation chromatography (GPC) chart of the copolymers obtained in Example 3 and Comparative Example 1.

The obtained polymer was easily dissolved in a general solvent such as THF and chloroform and had a number average molecular weight (Mn) of 560,000 and a molecular distribution (Mw/Mn) of 2.17. The composition ratio of the 2-acetoxymethyl-5-norbornene monomer unit in the polymer calculated by the integral value of the $^1$H-NMR spectrum was 24.1 mol %. $^1$H-NMR spectrum, IR spectrum and the gel permeation chromatography (GPC) chart are shown in FIG. 3, FIG. 4 and FIG. 5, respectively.

Examples 4 to 5

Addition Copolymerization of norbornene and 2-acetoxymethyl-5-norbornene

Polymerization was carried out in the same way as in Example 3 except that the polymerization temperature was changed to 80° C. in Example 4 and 90° C. in Example 5, as shown in Table 1.

Example 6

Addition copolymerization of norbornene and 2-acetoxymethyl-5-norbornene

Polymerization was carried out in the same way as in Example 4 except that cocatalyst (B) was changed from N,N-dimethylanilinium tetrakis(pentafluorophenyl)borate [($C_6$HO$(CH_3)_2$NH][B$(C_6F_5)_4$] to trityltetrakis(pentafluorophenyl)borate [($C_6H_5)_3$C][B$(C_6F_5)_4$] (manufactured by Tosoh Finechem Corporation, 9.2 mg, 0.010 mmol).

Example 7

Addition copolymerization of norbornene and 2-acetoxymethyl-5-norbornene

Polymerization was carried out in the same way as in Example 3 except that transition metal complex (A) was changed from (π-allyl){4-(2,6-diisopropylphenylimino)-2-penten-2-olato-$\kappa^2$N,O}palladium (Complex A-1) to (π-allyl){4-(1-naphthylimino)-2-penten-2-olato-$\kappa^2$N,O}palladium (Complex A-2) (3.7 mg, 0.010 mmol).

Examples 8 to 9

Addition copolymerization of norbornene and 2-acetoxymethyl-5-norbornene

Polymerization was carried out in the same way as in Example 7 except that the polymerization temperature was changed to 80° C. in Example 8 and 90° C. in Example 9 as shown in Table 1.

Example 10

Addition copolymerization of norbornene and 2-acetoxymethyl-5-norbornene

After the inside of a three-neck flask equipped with a three-way stopcock and a mechanical stirrer was substituted with nitrogen, norbornene (manufactured by Tokyo Chemical Industry Co., Ltd.; 7.06 g, 0.075 mol) and 2-acetoxymethyl-5-norbornene prepared in Synthesis Example 1 (24.93 g, 0.150 mol) were added thereto and dissolved in 110 ml of toluene. Further, a solution of N,N-dimethylanilinium tetrakis(pentafluorophenyl)borate [($C_6H_5)(CH_3)_2$NH][B$(C_6F_5)_4$] (manufactured by Tosoh Finechem Corporation, 8.0 mg, 0.010 mmol) dissolved in 1 ml of dichloromethane was added and heated to 70° C. After adding thereto a catalyst solution of (π-allyl){4-(1-naphthylimino)-2-penten-2-olato-$\kappa^2$N, O}palladium (Complex A-2) (3.7 mg, 0.010 mmol) synthesized in Synthesis Example 2 and prepared in another container and triisopropyl phosphine [P(i-$C_3H_7$)$_3$] (manufactured by Strem Chemicals, Inc.; 1.6 mg, 0.010 mmol) dissolved in 3.5 ml of toluene, polymerization reaction was carried out at 80° C. for 15 minutes. Subsequently, a solution of norbornene as prepared separately (Tokyo Chemical Industries Co., Ltd.; 7.06 g, 0.075 ml) dissolved in 8.2 ml of toluene was added thereto and the polymerization reaction was carried out at 80° C. for another 15 minutes. After the reaction was completed, 8 ml of methanol added with small quantity of hydrochloric acid was added to the reaction solution to thereby terminate the reaction. Next, the reaction solution was diluted with toluene and put into large quantity of methanol to precipitate polymers. The precipitated polymer was separated by filtration followed by washing, and then dried at 90° C. under reduced pressure for five hours to obtain 18.24 g of polymer in the white powder form. The catalytic activity calculated based on the polymer yield and the charge of the catalyst was 1,824 g of polymer/mmol of palladium (Pd).

The obtained polymer was easily dissolved in a general solvent such as THF and chloroform and had a number average molecular weight (Mn) of 312,000 and a molecular distribution (Mw/Mn) of 2.35. The composition ratio of the 2-acetoxymethyl-5-norbornene monomer unit in the polymer calculated by the integral value of the $^1$H-NMR spectrum was 23.9 mol %.

Example 11

Addition copolymerization of norbornene and 2-acetoxymethyl-5-norbornene (Precipitation Polymerization)

After the inside of a three-neck flask equipped with a three-way stopcock, a mechanical stirrer and a reflux condenser was substituted with nitrogen, a solution of norbornene (9.42 g, 0.100 mol) dissolved in 5.4 ml of toluene, and 2-acetoxymethyl-5-norbornene prepared in Synthesis Example 1 (16.62 g, 0.100 mol) were added thereto, dissolved in ethyl acetate (manufactured by SHOWA DENKO K.K., 70 ml) and heated in an oil bath of 80° C. Subsequently, a catalyst solution was added, which solution was obtained by adding a solution of N,N-dimethylanilinium tetrakis(pentafluorophenyl)borate [($C_6H_5$)($CH_3$)$_2$NH][B($C_6F_5$)$_4$] (manufactured by Tosoh Finechem Corporation; 8.0 mg, 0.010 mmol) dissolved in 1.0 ml of dichloromethane to a solution of (π-allyl){4-(1-naphthylimino)-2-penten-2-olato-κ$^2$N,O}palladium (Complex A-2) (3.7 mg, 0.010 mmol) synthesized in Synthesis Example 2 and prepared in another container and triisopropyl phosphine [P(i-$C_3H_7$)$_3$] (manufactured by Strem Chemicals, Inc.; 1.6 mg, 0.010 mmol) dissolved in 3.5 ml of toluene, to thereby carry out polymerization reaction while refluxing for one hour. During the polymerization, polymer was precipitated in white powder form. After the reaction was completed, 8 ml of methanol added with small quantity of hydrochloric acid was added to the reaction solution to thereby terminate the reaction. The precipitated polymer was separated by filtration followed by washing, and then dried at 90° C. under reduced pressure for five hours to obtain 11.46 g of polymer in the white powder form. The catalytic activity calculated based on the polymer yield and the charge of the catalyst was 1,146 g of polymer/mmol of palladium (Pd).

The obtained polymer was easily dissolved in a general solvent such as THF and chloroform and had a number average molecular weight (Mn) of 270,000 and a molecular distribution (Mw/Mn) of 2.24. The composition ratio of the 2-acetoxymethyl-5-norbornene monomer unit in the polymer calculated by the integral value of the $^1$H-NMR spectrum was 19.9 mol %.

Example 12

Addition copolymerization of norbornene and 2-acetoxymethyl-5-norbornene (Precipitation Polymerization)

After the inside of a three-neck flask equipped with a three-way stopcock, a mechanical stirrer and a reflux condenser was substituted with nitrogen, a solution of norbornene (9.42 g, 0.100 mol) dissolved in 5.4 ml of toluene, and 2-acetoxymethyl-5-norbornene prepared in Synthesis Example 1 (16.62 g, 0.100 mol) were added thereto, dissolved in ethyl acetate (manufactured by SHOWA DENKO K.K., 70 ml) and heated in an oil bath of 80° C. Then a catalyst solution was added, which solution was obtained by adding a solution of N,N-dimethylanilinium tetrakis(pentafluorophenyl)borate [($C_6H_5$)($CH_3$)$_2$NH][B($C_6F_5$)$_4$] (manufactured by Tosoh Finechem Corporation; 8.0 mg, 0.010 mmol) dissolved in 1.0 ml of dichloromethane to a solution of (π-allyl){4-(1-naphthylimino)-2-penten-2-olato-κ$^2$N,O}palladium (Complex A-2) (3.7 mg, 0.010 mmol) synthesized in Synthesis Example 2 and prepared in another container and triisopropyl phosphine [P(i-$C_3H_7$)$_3$] (manufactured by Strem Chemicals, Inc.; 1.6 mg, 0.010 mmol) dissolved in 3.5 ml of toluene, to thereby carry out polymerization reaction while refluxing for 15 minutes. Subsequently, a solution of norbornene as prepared separately (Tokyo Chemical Industries Co., Ltd.; 9.42 g, 0.100 ml) dissolved in 8.2 ml of toluene and 2-acetoxymethyl-5-norbornene (5.57 g, 0.034 mol) were added thereto and the polymerization reaction was carried out while refluxing for another 15 minutes. During the polymerization, polymer was precipitated in the white powder form. After the reaction was completed, 8 ml of methanol added with small quantity of hydrochloric acid was added to the reaction solution to thereby terminate the reaction. The precipitated polymer was separated by filtration followed by washing, and then dried at 90° C. under reduced pressure for five hours to obtain 18.97 g of polymer in the white powder form. The catalytic activity calculated based on the polymer yield and the charge of the catalyst was 1,897 g of polymer/mmol of palladium (Pd).

The obtained polymer was easily dissolved in a general solvent such as THF and chloroform and had a number average molecular weight (Mn) of 335,000 and a molecular distribution (Mw/Mn) of 2.47. The composition ratio of the 2-acetoxymethyl-5-norbornene monomer unit in the polymer calculated by the integral value of the $^1$H-NMR spectrum was 16.7 mol %.

Example 13

Addition homopolymerization of 2-acetoxymethyl-5-norbornene

After the inside of a three-neck flask equipped with a three-way stopcock and a mechanical stirrer was substituted with nitrogen, 2-acetoxymethyl-5-norbornene prepared in Synthesis Example 1 (16.62 g, 0.100 mol) was added thereto. After further adding thereto a solution of N,N-dimethylanilinium tetrakis(pentafluorophenyl)borate [($C_6$HO($CH_3$)$_2$NH][B($C_6F_5$)$_4$] (manufactured by Tosoh Finechem Corporation; 8.0 mg, 0.010 mmol) dissolved in 1 ml of dichloromethane, the resultant solution was heated to 80° C. Then, adding thereto a catalyst solution of (π-allyl){4-(1-naphthylimino)-2-penten-2-olato-κ²N,O}palladium (Complex A-2) (3.7 mg, 0.010 mmol) synthesized in Synthesis Example 2 and prepared in another container and triisopropyl phosphine [P(i-C₃H₇)₃] (manufactured by Strem Chemicals, Inc.; 1.6 mg, 0.010 mmol) dissolved in 3.5 ml of toluene, the polymerization reaction was performed at 80° C. for 60 minutes. After the reaction was completed, 8 ml of methanol added with small quantity of hydrochloric acid was added to the reaction solution to thereby terminate the reaction. Next, the reaction solution was diluted with toluene and put into large quantity of methanol to precipitate polymers. The precipitated polymer was separated by filtration followed by washing, and then dried at 90° C. under reduced pressure for five hours to obtain 6.43 g of polymer in the white powder form. The catalytic activity calculated based on the polymer yield and the charge of the catalyst was 643 g of polymer/mmol of palladium (Pd).

Figure 6:
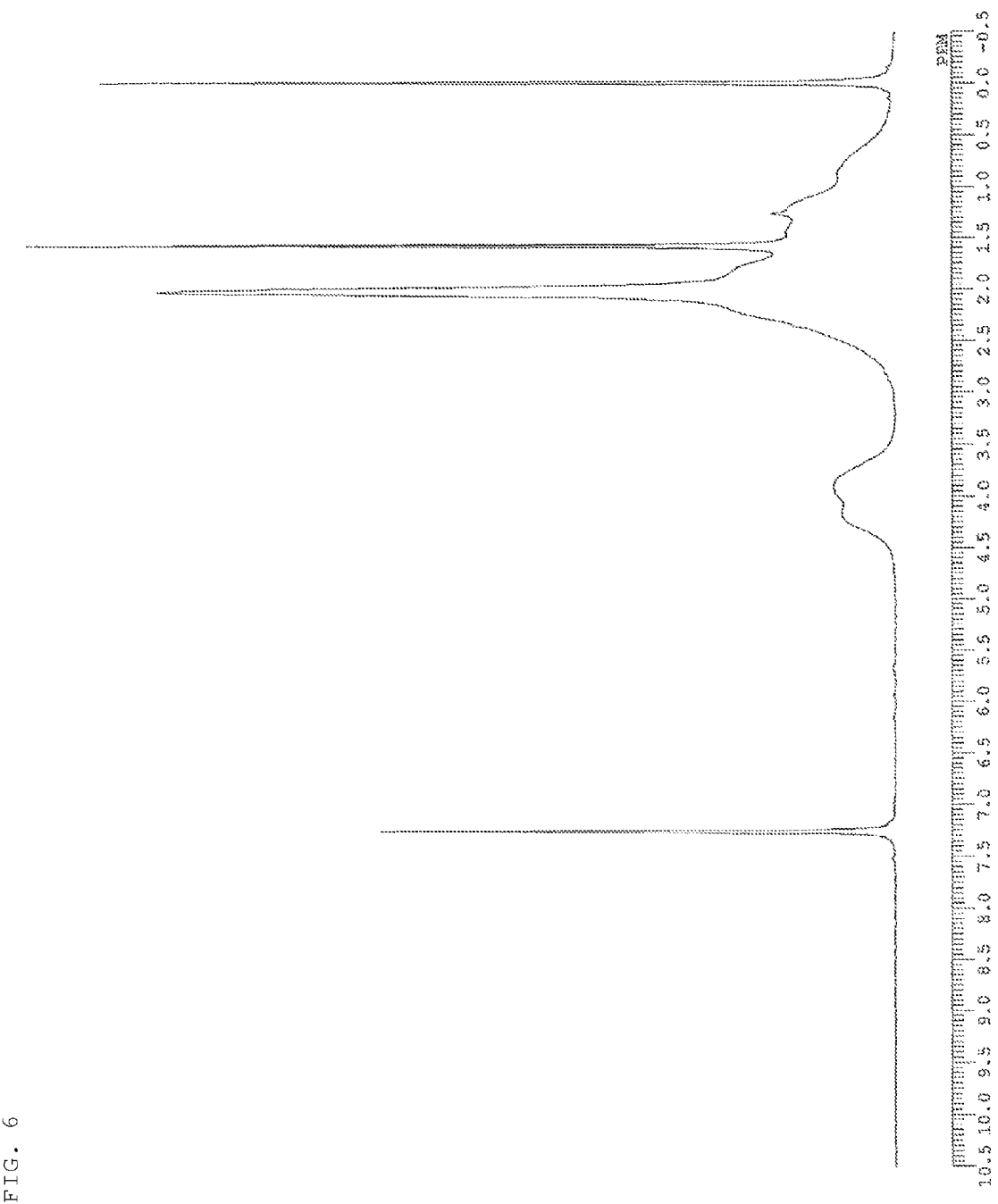
FIG. 6 is a $^1$H-NMR spectrum of the homopolymer obtained in Example 13.
Figure 7:
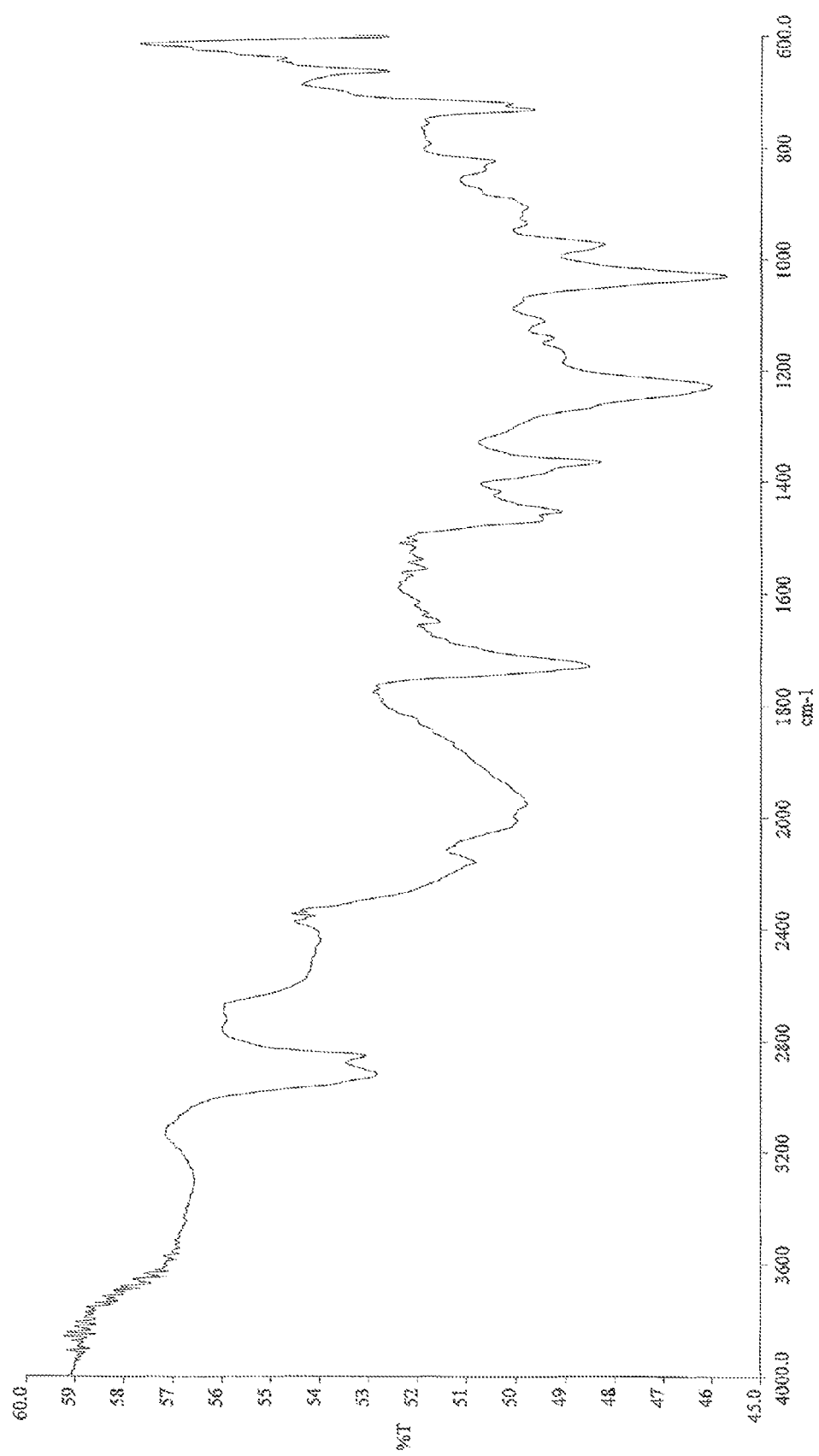
FIG. 7 is an IR spectrum of the homopolymer obtained in Example 13.
Figure 8:
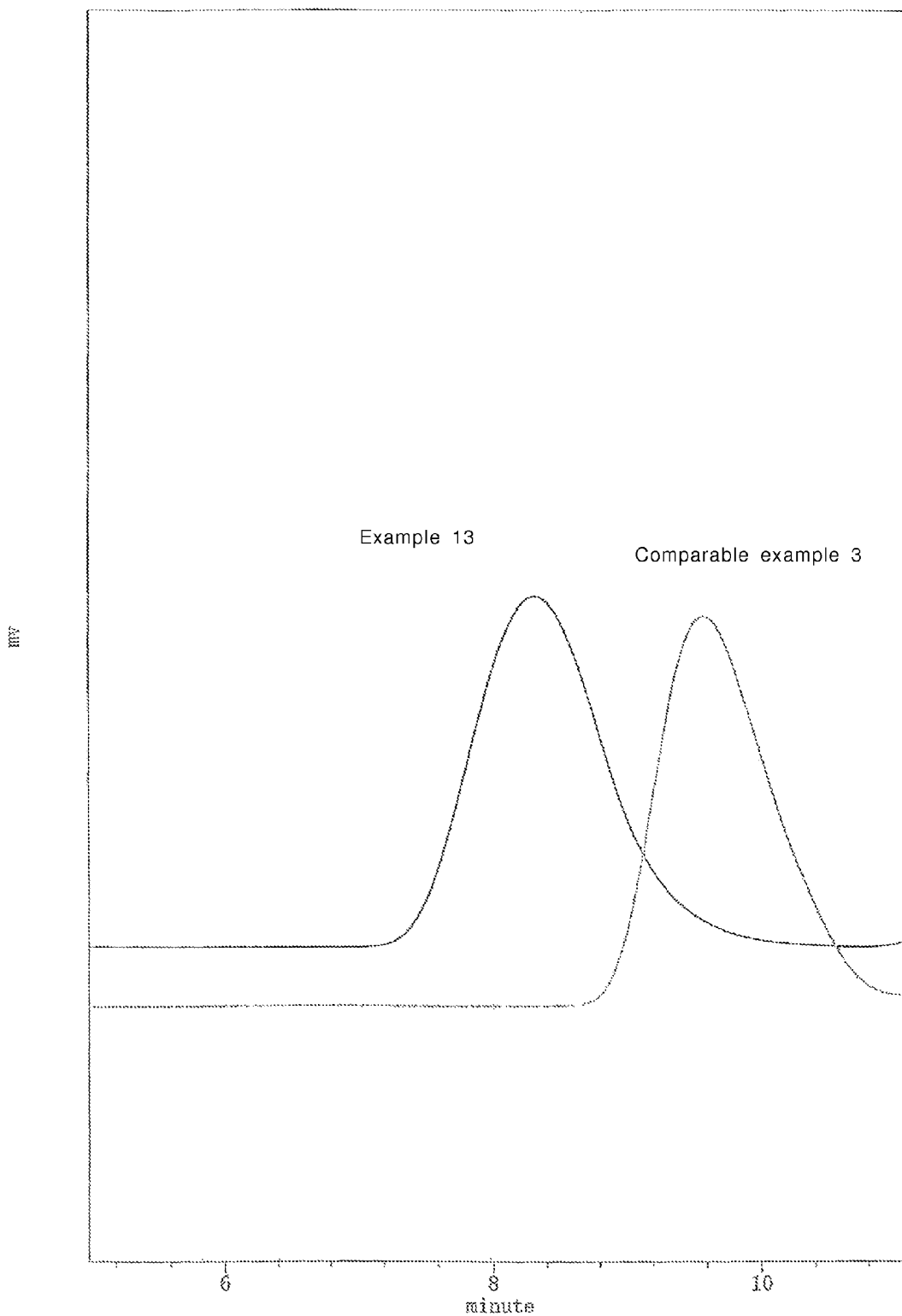
FIG. 8 is a gel permeation chromatography (GPC) chart of the homopolymers obtained in Example 13 and Comparative Example 3.

The obtained polymer was easily dissolved in a general solvent such as THF and chloroform and had a number average molecular weight (Mn) of 208,000 and a molecular distribution (Mw/Mn) of 2.24. ¹H-NMR spectrum, IR spectrum and the gel permeation chromatography (GPC) chart are shown in FIG. 6, FIG. 7 and FIG. 8, respectively.

Example 14

Polymerization was carried out in the same way as in Example 13 except that the polymerization temperature was changed from 80° C. to 70° C.

Example 15

Addition homopolymerization of 2-acetoxymethyl-5-norbornene

After the inside of a three-neck flask equipped with a three-way stopcock and a mechanical stirrer was substituted with nitrogen, 2-acetoxymethyl-5-norbornene prepared in Synthesis Example 1 (16.62 g, 0.100 mol) was added thereto and heated to 80° C. Further adding a catalyst solution in which a solution of N,N-dimethylanilinium tetrakis(pentafluorophenyl)borate [(C₆H₅)(CH₃)₂NH][B(C₆F₅)₄] (manufactured by Tosoh Finechem Corporation; 8.0 mg, 0.010 mmol) dissolved in 1 ml of dichloromethane was added to a solution of (π-allyl){4-(1-naphthylimino)-2-penten-2-olato-κ²N,O}palladium (Complex A-2) (3.7 mg, 0.010 mmol) synthesized in Synthesis Example 2 and prepared in another container and triisopropyl phosphine [P(i-C₃H₇)₃] (manufactured by Strem Chemicals, Inc.; 1.6 mg, 0.010 mmol) dissolved in 3.5 ml of toluene, the polymerization reaction was performed at 80° C. for 60 minutes. After the reaction was completed, 8 ml of methanol added with small quantity of hydrochloric acid was added to the reaction solution to thereby terminate the reaction. Next, the reaction solution was diluted with toluene and put into large quantity of methanol to precipitate polymers. The precipitated polymer was separated by filtration followed by washing, and then dried at 90° C. under reduced pressure for five hours to obtain 7.00 g of polymer in the white powder form. The catalytic activity calculated based on the polymer yield and the charge of the catalyst was 700 g of polymer/mmol of palladium (Pd).

The obtained polymer was easily dissolved in a general solvent such as THF and chloroform and had a number average molecular weight (Mn) of 229,000 and a molecular distribution (Mw/Mn) of 2.09.

Comparative Example 1

Addition copolymerization of norbornene and 2-acetoxymethyl-5-norbornene (Polymerization According to the Method of Patent Document 4)

After the inside of a two-neck flask equipped with a three-way stopcock was substituted with nitrogen, 2-acetoxymethyl-5-norbornene prepared in Synthesis Example 1 (14.13 g, 0.085 mol) was added thereto and dissolved in 50 ml of toluene. After further adding thereto a solution of allylpalladium chloride dimer [[(C₃H₅)PdCl]₂] (manufactured by Wako Pure Chemical Industries Co., Ltd., 9 mg, 0.025 mmol) dissolved in 1 ml of toluene, a solution of tricyclohexylphosphine [P(C₆H₁₁)₃] (manufactured by Strem Chemicals Inc.; 14 mg, 0.050 mmol) dissolved in 1 ml of toluene and a solution of N,N-dimethylanilinium tetrakis(pentafluorophenyl)borate [(C₆HO(CH₃)₂NH][B(C₆F₅)₄] (manufactured by Strem Chemicals Inc., 60 mg, 0.075 mmol) dissolved in 1 ml of dichloromethane separately in that order, the flask was dipped in an oil bath and heated to 90° C. while being stirred. A solution of norbornene (manufactured by Tokyo Chemical Industries Co., Ltd.; 8.00 g, 0.085 mol) as prepared separately dissolved in 10 ml of toluene was added to the flask to thereby initiate polymerization reaction, and polymerization reaction was performed at 90° C. for two hours. After the reaction was completed, the reaction solution was put into large quantity of methanol to thereby precipitate polymers. The precipitated polymer was separated by filtration followed by washing, and then dried at 60° C. under reduced pressure for five hours to obtain 19.4 g of polymer in the white powder form. The catalytic activity calculated based on the polymer yield and the charge of the catalyst was 388 g of polymer/mmol of palladium (Pd).

The obtained polymer was easily dissolved in a general solvent such as THF and chloroform and had a number average molecular weight (Mn) of 58,000 and a molecular distribution (Mw/Mn) of 2.06. The composition ratio of the 2-acetoxymethyl-5-norbornene monomer unit in the polymer calculated by the integral value of the ¹H-NMR spectrum was 37.3 mol %.

Comparative Example 2

Addition copolymerization of norbornene and 2-acetoxymethyl-5-norbornene (Polymerization According to the Method of Patent Document 4)

Polymerization was carried out in the same way as in Comparative Example 1 except that allylpalladium chloride dimer [[(C₃H₅)PdCl]₂] (4.5 mg, 0.0125 mmol), tricyclohexylphosphine [P(C₆H₁₁)₃] (7 mg, 0.025 mmol) and N,N-dimethylanilinium tetrakis(pentafluorophenyl)borate [(C₆HO(CH₃)₂NH][B(C₆F₅)₄] (30 mg, 0.0375 mmol) were used as a catalyst and the reaction was performed at 60° C. to obtain 4.3 g of polymer in the white powder form. The catalytic activity calculated based on the polymer yield and the charge of the catalyst was 172 g of polymer/mmol of palladium (Pd).

The obtained polymer was easily dissolved in a general solvent such as THF and chloroform and had a number average molecular weight (Mn) of 105,400 and a molecular distribution (Mw/Mn) of 1.98. The composition ratio of the 2-acetoxymethyl-5-norbornene monomer unit in the polymer calculated by the integral value of the ¹H-NMR spectrum was 18.2 mol %.

Comparative Example 3

Addition homopolymerization of 2-acetoxymethyl-5-norbornene (Polymerization According to the Method of Patent Document 4)

After the inside of a two-neck flask equipped with a three-way stopcock was substituted with nitrogen, 2-acetoxymethyl-5-norbornene prepared in Synthesis Example 1 (14.13 g, 0.085 mol) was added thereto and dissolved in 67 ml of toluene. After further adding thereto a solution of allylpalladium chloride dimer [[C₃H₅PdCl]₂] (manufactured by Wako Pure Chemical Industries Co., Ltd., 4.5 mg, 0.0125 mmol) dissolved in 1 ml of toluene, a solution of tricyclohexylphosphine [P(C$_6$H$_{11}$)$_3$] (manufactured by Strem Chemicals Inc.; 7 mg, 0.025 mmol) dissolved in 1 ml of toluene and a solution of N,N-dimethylaniliniumtetrakis(pentafluorophenyl)borate [(C$_6$HO(CH$_3$)$_2$NH][B(C$_6$F$_5$)$_4$] (manufactured by Strem Chemicals Inc., 30 mg, 0.0375 mmol) dissolved in 1 ml of dichloromethane separately in that order, the flask was dipped in an oil bath and heated to 90° C. while stirring to thereby carry out polymerization reaction for two hours. After the reaction was completed, the reaction solution was put into large quantity of methanol to thereby precipitate polymers. The precipitated polymer was separated by filtration followed by washing, and then dried at 60° C. under reduced pressure for five hours to obtain 0.35 g of polymer in the white powder form. The catalytic activity calculated based on the polymer yield and the charge of the catalyst was 14 g of polymer/mmol of palladium (Pd).

The obtained polymer was easily dissolved in a general solvent such as THF and chloroform and had a number average molecular weight (Mn) of 26,000 and a molecular distribution (Mw/Mn) of 1.86.

Comparative Example 4

Addition homopolymerization of 2-acetoxymethyl-5-norbornene (Polymerization According to the Method of Non-patent Document 1)

Non-patent Document 1 describes a method as follows. That is, as general reaction conditions, the document has the description that a solution of [(1,2,3-η)-1,1-diphenyl-2-methyl-2-propenyl]chloro[1,3-bis(2,6-diisopropylphenyl)-2-imidazolidene]palladium (1.6 mg, 0.0022 mmol) and lithium tetrakis(pentafluorophenyl)borate.diethyl ether complex, Li[B(C$_6$F$_5$)$_4$.2.5(C$_2$H$_5$)$_2$O] (3.0 mg, 0.0034 mmol) dissolved in chlorobenzene (3 ml) was reacted under nitrogen atmosphere at room temperature for eight hours. Subsequently, the reaction solution was filtrated through a syringe filter, and the filtrate was added to a solution of 5-acetoxymethyl-2-norbornene (1.0 g, 6.6 mmol) dissolved in chlorobenzene (1 ml) as prepared separately. Next, the resultant solution was reacted at a predetermined temperature for 20 hours, and the powder obtained by reprecipitation in methanol (50 ml) was washed with methanol (20 ml) three times and further dried in vacuum. Non-patent Document 1 does not describe details on each of the production methods, but teaches in Table 3 that in the case when setting the reaction time of one hour, charging [(1,2,3-η)-1,1-diphenyl-2-methyl-2-propenyl]chloro[1,3-bis (2,6-diisopropylphenyl)-2-imidazolidene]palladium in an amount of two thousandth of 5-acetoxymethyl-2-norbornene by molar ratio and lithium tetrakis(pentafluorophenyl)borate.diethyl ether complex, Li[B(C$_6$F$_5$)$_{4\text{-}2.5}$(C$_2$H$_5$)$_2$O], in an amount of 1.5 times palladium complex by molar ratio, using chlorobenzene as a solvent and controlling the reaction temperature to 50° C., a polymer was obtained, in which a catalytic activity calculated based on the polymer yield and the charge of the catalyst was 123 g of polymer/mmol of palladium (Pd) and a number average molecular weight (Mn) was 65,000.

Comparative Example 5

Addition homopolymerization of 2-acetoxymethyl-5-norbornene (Polymerization According to the Method of Non-patent Document 1)

Non-patent Document 1 teaches in Table 3 that in the case when setting the reaction time of four hours, charging [(1,2, 3-η)-1,1-diphenyl-2-methyl-2-propenyl]chloro[1,3-bis(2,6-diisopropylphenyl)-2-imidazolidene]palladium in an amount of two thousandth of 5-acetoxymethyl-2-norbornene by molar ratio and lithium tetrakis(pentafluorophenyl)borate.diethyl ether complex, Li[B(C$_6$F$_5$)$_4$.2.5(C$_2$H$_5$)$_2$O], in an amount of 1.5 times palladium complex by molar ratio, using chlorobenzene as a solvent and controlling the reaction temperature to 50° C., a polymer was obtained, in which a catalytic activity calculated based on the polymer yield and the charge of the catalyst was 60 g of polymer/mmol of palladium (Pd) and a number average molecular weight (Mn) was 126, 000.

With respect to Examples 3 to 15 and Comparative Examples 1 to 5, type of the catalyst, polymerization conditions and the like are shown in Table 1 and the polymerization results are shown in Table 2. Each of the symbols in Table 1 has the meaning as follows:

Metal Complex (A):
  A-1: (π-allyl){4-(2,6-diisopropylphenylimino)-2-penten-2-olato-κ$^2$N,O}palladium
  A-2: (π-allyl){4-[1-naphthylimino]-2-penten-2-olato-κ$^2$N,O}palladium
  CA-1: allylpalladium chloride dimer
  CA-2: [(1,2,3-η)-1,1-diphenyl-2-methyl-2-propenyl]chloro[1,3-bis(2,6-diisopropylphenyl)-2-imidazolidene]palladium Cocatalyst (B):
  B-1: N,N-dimethylaniliniumtetrakis(pentafluorophenyl)borate,
  B-2: trityltetrakis(pentafluorophenyl)borate,
  B-3: lithium tetrakis(pentafluorophenyl)borate Phosphine Ligand (C)
  C-1: triisopropylphosphine,
  C-2: tricyclohexylphosphine, Monomer:
NB: norbornene,
ANB: 2-acetoxymethyl-5-norbornene All the polymers obtained in Examples 3 to 15 and Comparative Examples 1 to 3 were easily dissolved in a general solvent such as THF and chloroform.

TABLE 1

| | | | | | | | | | Polymerization conditions | |
| | | catalyst | | | | | monomer | | polymeri- | |
| | metal complex (A) | | cocatalyst (B) | | Phosphine ligand (C) | | charge of monomer | | additional charge of monomer | | zation temp- | Polymeri- |
| | type | [mg] | type | [mg] | type | [mg] | NB [g] | ANB [g] | NB [g] | ANB [g] | ature [° C.] | zation time [min] |
|---|---|---|---|---|---|---|---|---|---|---|---|---|
| Example 3 | A-1 | 4.1 | B-1 | 8.0 | C-1 | 1.6 | 4.71 | 16.62 | 4.71 × 1 | — | 70 | 30 × 2 = 60 |
| Example 4 | ↑ | ↑ | ↑ | ↑ | ↑ | ↑ | ↑ | ↑ | ↑ | — | 80 | 30 × 2 = 60 |
| Example 5 | ↑ | ↑ | ↑ | ↑ | ↑ | ↑ | ↑ | ↑ | ↑ | — | 90 | 30 × 2 = 60 |
| Example 6 | ↑ | ↑ | B-2 | 9.2 | ↑ | ↑ | ↑ | ↑ | ↑ | — | 80 | 30 × 2 = 60 |
| Example 7 | A-2 | 3.7 | B-1 | 8.0 | ↑ | ↑ | ↑ | ↑ | ↑ | — | 70 | 30 × 2 = 60 |

TABLE 1-continued

| | catalyst | | | | | | monomer | | | | Polymerization conditions | |
|---|---|---|---|---|---|---|---|---|---|---|---|---|
| | metal complex (A) | | cocatalyst (B) | | Phosphine ligand (C) | | charge of monomer | | additional charge of monomer | | polymerization temperature | Polymerization time |
| | | | | | | | NB | ANB | NB | ANB | | |
| | type | [mg] | type | [mg] | type | [mg] | [g] | [g] | [g] | [g] | [° C.] | [min] |
| Example 8 | ↑ | ↑ | ↑ | ↑ | ↑ | ↑ | ↑ | ↑ | ↑ | — | 80 | 30 × 2 = 60 |
| Example 9 | ↑ | ↑ | ↑ | ↑ | ↑ | ↑ | ↑ | ↑ | ↑ | — | 90 | 30 × 2 = 60 |
| Example 10 | ↑ | ↑ | ↑ | ↑ | ↑ | ↑ | 7.06 | 24.93 | 7.06 × 1 | — | 80 | 15 × 2 = 30 |
| Example 11 | ↑ | ↑ | ↑ | ↑ | ↑ | ↑ | 9.42 | 16.62 | — | — | ↑ | 60 × 1 = 60 |
| Example 12 | ↑ | ↑ | ↑ | ↑ | ↑ | ↑ | ↑ | ↑ | 9.42 × 1 | 5.57 × 1 | ↑ | 15 × 2 = 30 |
| Example 13 | ↑ | ↑ | ↑ | ↑ | ↑ | ↑ | — | ↑ | — | — | 80 | 60 × 1 = 60 |
| Example 14 | ↑ | ↑ | ↑ | ↑ | ↑ | ↑ | — | ↑ | — | — | 70 | 60 × 1 = 60 |
| Example 15* | ↑ | ↑ | ↑ | ↑ | ↑ | ↑ | — | ↑ | — | — | 80 | 60 × 1 = 60 |
| Comp. Ex. 1 | CA-1 | 9.0 | ↑ | 60.0 | C-2 | 14.0 | 8.00 | 14.13 | — | — | 90 | 120 × 1 = 120 |
| Comp. Ex. 2 | ↑ | 4.5 | ↑ | 30.0 | ↑ | 7.0 | ↑ | ↑ | — | — | 60 | 120 × 1 = 120 |
| Comp. Ex. 3 | ↑ | ↑ | ↑ | ↑ | ↑ | ↑ | — | ↑ | — | — | 90 | 120 × 1 = 120 |
| Comp. Ex. 4 | CA-2 | — | B-3 | — | — | — | — | — | — | — | 50 | 60 × 1 = 60 |
| Comp. Ex. 5 | ↑ | — | ↑ | — | — | — | — | — | — | — | 50 | 240 × 1 = 240 |

*The order of mixing the catalyst is different from that of Example 13.

TABLE 2

| | Polymerization results | | | | | |
|---|---|---|---|---|---|---|
| | polymer yield | catalytic activity | Molecular weight | | | ANB content |
| | [g] | [g/mmol] | Mn | Mw | Mw/Mn | [mol %] |
| Example 3 | 8.73 | 873 | 560,000 | 1,220,000 | 2.17 | 24.1 |
| Example 4 | 11.16 | 1116 | 376,000 | 906,000 | 2.41 | 22.7 |
| Example 5 | 11.46 | 1146 | 303,000 | 830,000 | 2.74 | 27.8 |
| Example 6 | 13.44 | 1344 | 578,000 | 1,352,000 | 2.34 | 24.6 |
| Example 7 | 14.39 | 1439 | 405,000 | 1,000,000 | 2.48 | 27.0 |
| Example 8 | 14.46 | 1446 | 253,000 | 625,000 | 2.47 | 26.1 |
| Example 9 | 16.66 | 1666 | 128,000 | 348,000 | 2.72 | 29.7 |
| Example 10 | 18.24 | 1824 | 312,000 | 733,000 | 2.35 | 23.9 |
| Example 11 | 11.46 | 1146 | 270,000 | 605,000 | 2.24 | 19.9 |
| Example 12 | 18.97 | 1897 | 335,000 | 827,000 | 2.47 | 16.7 |
| Example 13 | 6.43 | 643 | 208,000 | 466,000 | 2.24 | 100.0 |
| Example 14 | 4.86 | 486 | 247,000 | 482,000 | 1.95 | 100.0 |
| Example 15 | 7.00 | 700 | 229,000 | 479,000 | 2.09 | 100.0 |
| Comparative Ex. 1 | 19.40 | 388 | 58,000 | 120,000 | 2.06 | 37.3 |
| Comparative Ex. 2 | 4.30 | 172 | 105,400 | 210,000 | 1.98 | 18.2 |
| Comparative Ex. 3 | 0.35 | 14 | 26,000 | 50,000 | 1.86 | 100.0 |
| Comparative Ex. 4 | — | 123 | 65,000 | 134,000 | 2.05 | 100.0 |
| Comparative Ex. 5 | — | 60 | 126,000 | 199,000 | 1.57 | 100.0 |

Regarding copolymerization, a copolymer having a molecular weight (Mn) exceeding 200,000 has not been produced by the method of Patent Document 4, and the catalytic activity having prospect of industrially practical use was not confirmed (Comparative Examples 1 to 2). According to the production method of the present invention, norbornene copolymers having excellent mechanical properties and molecular weight (Mn) exceeding 200,000 was obtained with the catalytic activity having prospect of industrially practical use (Examples 3 to 15).

On the other hand, regarding homopolymerization, a homopolymer having a molecular weight (Mn) exceeding 200,000 has not been produced by the method of Non-patent Document 1, and the catalytic activity having prospect of industrially practical use was not confirmed even in the case of homopolymer having molecular weight (Mn) less than 200,000 (Comparative Examples 3). According to the method for producing norbornene homopolymer of the present invention, polymers having molecular weight (Mn) exceeding 200,000 was obtained with the catalytic activity having prospect of industrially practical use (Examples 13 to 15).

INDUSTRIAL APPLICABILITY

The norbornene (co)polymer obtained by the production method of the present invention has excellent properties such as transparency, heat resistance, low water absorption and electric insulating property, and can be used for optical molded products such as lenses and polarizing films; films, carrier tapes, film capacitors, electric insulating materials for flexible printed circuit boards and the like; and medical containers such as press-through packages, infusion bags and chemical vials; food-packaging molded product such as plastic wraps and trays; casings for electric appliances; automobile interior parts such as an inner panel; building materials for a carport, glazing and the like; etc.

The invention claimed is:

1. A catalyst for the polymerization of norbornene monomers, comprising (i) transition metal complex (A) represented by formula (1)

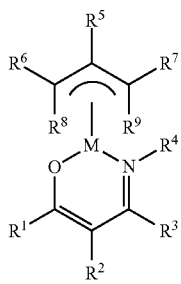

(1)

wherein M represents one transition metal selected from the elements belonging to eight, nine or ten group of the periodic table for 1991, and $R^1$, $R^2$ and $R^3$ independently represent a hydrogen atom or a hydrocarbon group having 1 to 20 carbon atoms; $R^4$ represents a hydrogen atom or a hydrocarbon group having 1 to 20 carbon atoms; $R^5$, $R^6$, $R^7$, $R^8$ and $R^9$ represent independently from each other a hydrogen atom, a halogen atom or a hydrocarbon group having 1 to 20 carbon atoms; and $R^5$, $R^6$, $R^7$, $R^8$ and $R^9$ may bond to each other to form a ring structure, and (ii) cocatalyst (B) which is an ionic compound which can generate a cationic transition metal compound by reacting with transition metal complex (A) and a phosphine ligand (C).

2. The catalyst for the polymerization of norbornene monomers as claimed in claim 1, wherein M represents palladium (Pd) or nickel (Ni); $R^1$, $R^2$ and $R^3$ represents a hydrogen atom or an alkyl group having 1 to 6 carbon atoms; $R^4$ represents an aryl group having 6 to 20 carbon atoms; and all of $R^5$, $R^6$, $R^7$, $R^8$ and $R^9$ represent a hydrogen atom in formula (1).

3. The catalyst for the polymerization of norbornene monomers as claimed in claim 2, wherein M represents palladium; $R^1$ and $R^3$ represent a methyl group; $R^2$ represents a hydrogen atom; and $R^4$ represent a 2,6-diisopropylphenyl group or a 1-naphthyl group in formula (1).

4. The catalyst for the polymerization of norbornene monomers as claimed in claim 1, wherein cocatalyst (B) is trityl tetrakis(pentafluorophenyl)borate or N,N-dimethylanilinium tetrakis(pentafluorophenyl)borate.

5. The catalyst for the polymerization of norbornene monomers as described in claim 1, wherein phosphine ligand (C) is trialkylphosphine.

6. The catalyst for the polymerization of norbornene monomers as claimed in claim 5, wherein phosphine ligand (C) is triisopropylphosphine.

7. A method for producing norbornene (co)polymers comprising homopolymerization of norbornene monomers alone or copolymerization of norbornene monomers in the presence of the catalyst as claimed in claim 1.

8. A method for producing norbornene copolymers comprising copolymerization of norbornene monomers and other vinyl monomers in the presence of the catalyst as claimed in claim 1.

9. A method for producing norbornene copolymers comprising monomer units represented by formulae (2) and (3),

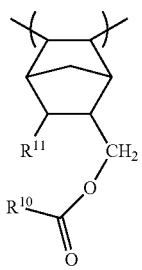

(2)

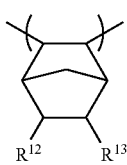

(3)

wherein $R^{10}$ represents an alkyl group having 1 to 10 carbon atoms; and $R^{11}$, $R^{12}$ and $R^{13}$ independently represent a hydrogen atom or an alkyl group having 1 to 10 carbon atoms, comprising polymerization of norbornene monomers corresponding to the monomer unit represented by formulae (2) and (3) in the presence of the catalyst as claimed in claim 1.

10. The method for producing norbornene copolymers as claimed in claim 9, wherein the copolymers comprise a monomer unit represented by formulae (2) and (3) only.

11. (π-allyl){4-(2,6-diisopropylphenylimino)-2-penten-2-olato-κ²N,O}palladium.

12. (π-allyl){4-(1-naphthylimino)-2-penten-2-olato-κ²N,O}palladium.

* * * * *